United States Patent [19]
Bechtel et al.

[11] Patent Number: 5,503,024
[45] Date of Patent: Apr. 2, 1996

[54] APPARATUS FOR TESTING LUMBER STIFFNESS

[75] Inventors: Friend K. Bechtel, Moscow, Id.;
Ronnie K. Byers, Pullman, Wash.;
James D. Logan, Pullman, Wash.;
James R. Allen, Pullman, Wash.;
Michael G. Strevy, Colfax, Wash.;
Daniel A. Uskoski, Pullman, Wash.

[73] Assignee: Metriguard Inc., Pullman, Wash.

[21] Appl. No.: 363,660

[22] Filed: Dec. 22, 1994

[51] Int. Cl.[6] .................................................. G01N 3/20
[52] U.S. Cl. ................................. 73/852; 73/849
[58] Field of Search ........................ 73/849, 852, 853, 73/856

[56] References Cited

U.S. PATENT DOCUMENTS

| | | | |
|---|---|---|---|
| 3,196,672 | 7/1965 | Keller | 73/100 |
| 4,708,020 | 11/1987 | Lau et al. | 73/852 |
| 4,852,029 | 7/1989 | Pope et al. | 73/852 |
| 4,932,267 | 6/1990 | Bechtel | 73/852 |
| 4,991,446 | 2/1991 | Bechtel | 73/849 |
| 5,074,244 | 12/1991 | Byers | 118/669 |

OTHER PUBLICATIONS

Metriguard Inc. Brochure, "CLT–Continuous Lumber Tester".
Logan, James D. "Getting Started with Machine Stress Rating".
Bechtel, F. K. "Machine Stress Rating with the CLT Continuous Lumber Tester".
Bechtel, F. K. "Feasibility of MSR Lumber Production".

Primary Examiner—Richard Chilcot
Assistant Examiner—Max Noori

[57] ABSTRACT

Improved apparatus is described for measuring bending stiffness of dimension lumber. Innovative details are introduced that make the measurement more accurate and repeatable as well as making the apparatus simpler, more robust and easier to maintain than the prior art.

19 Claims, 18 Drawing Sheets

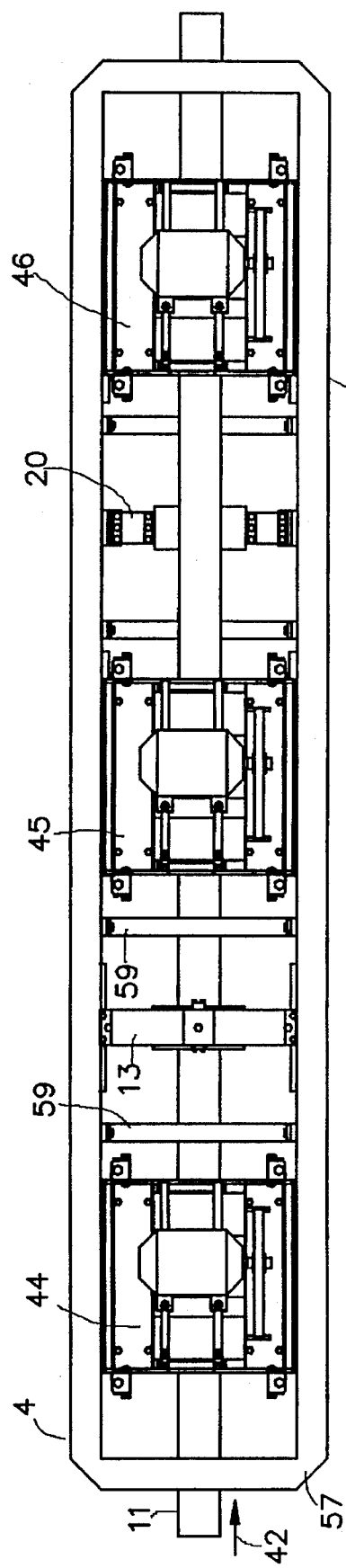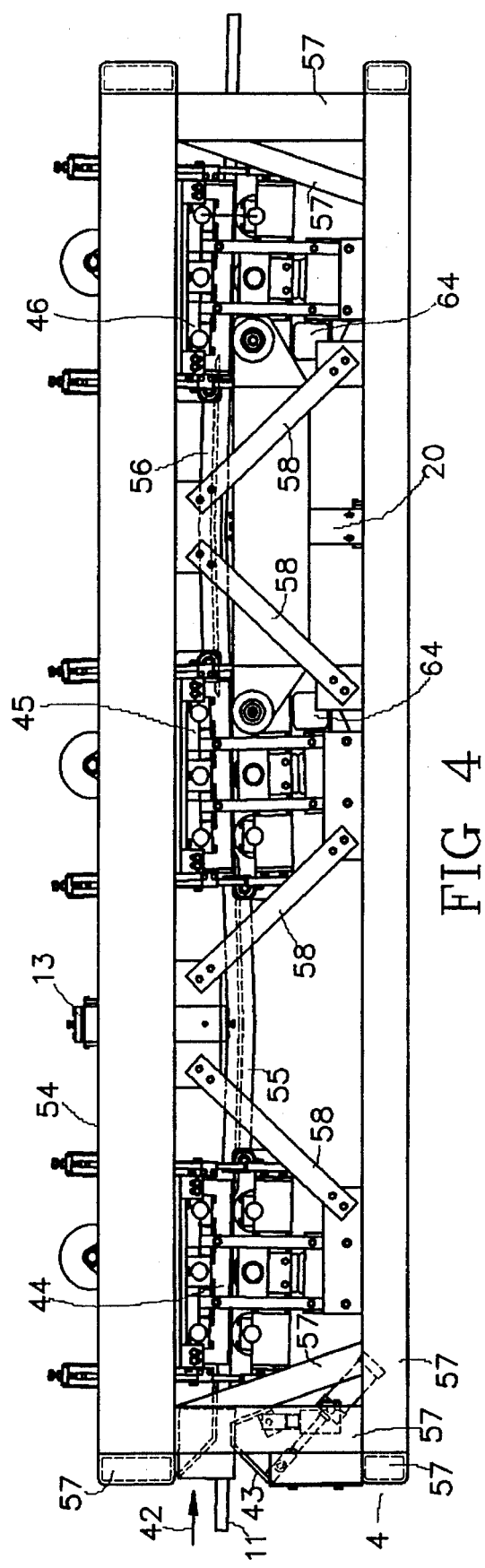

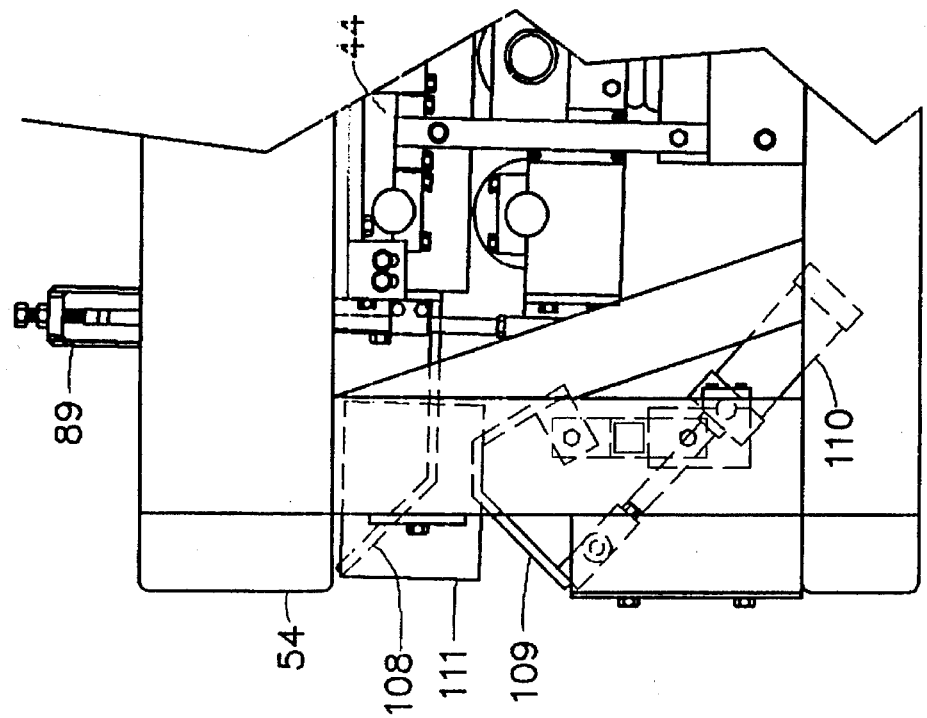
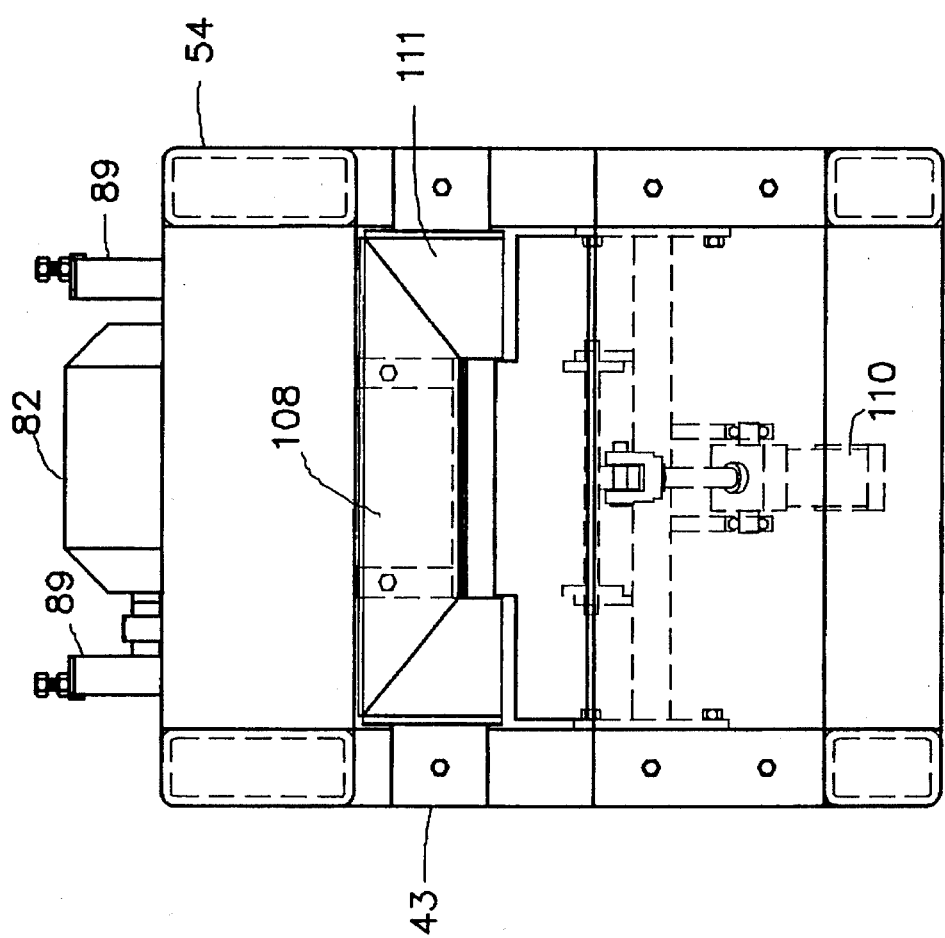

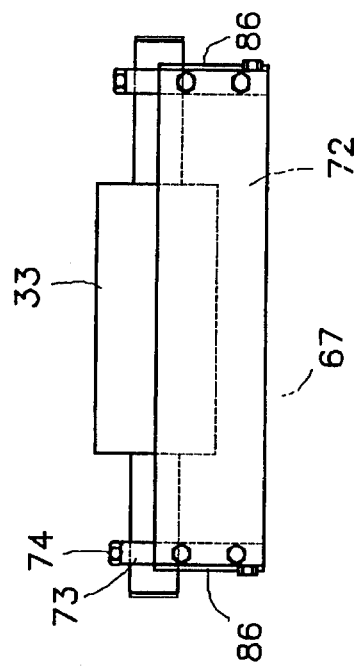
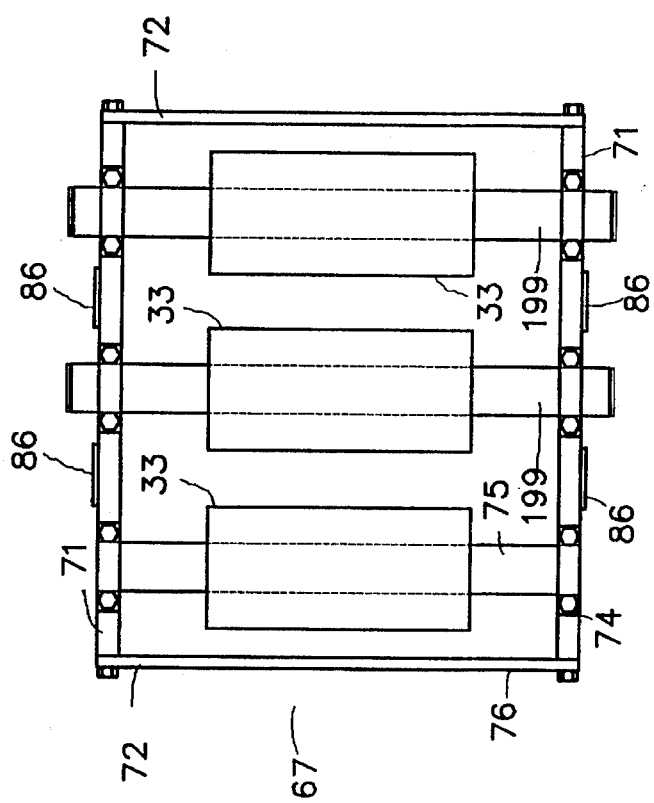
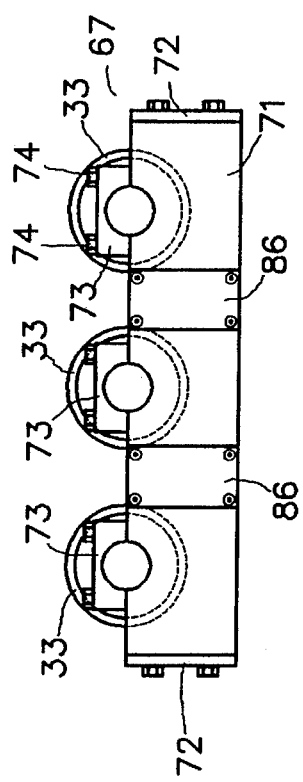

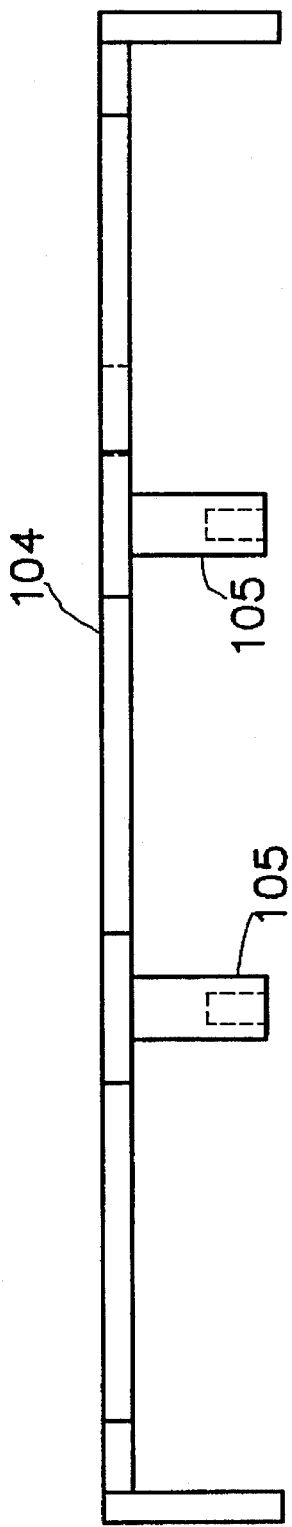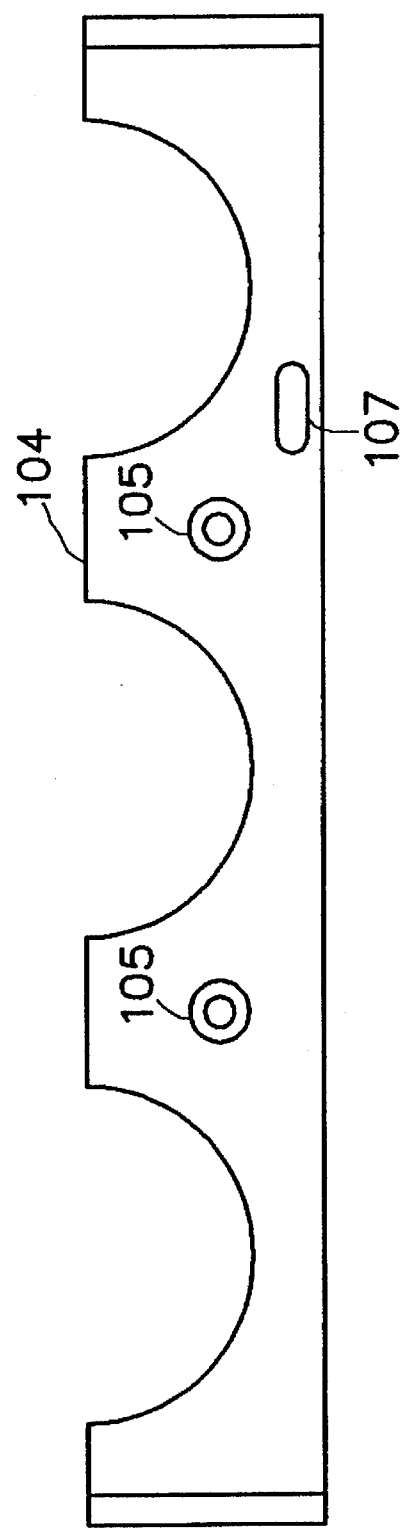

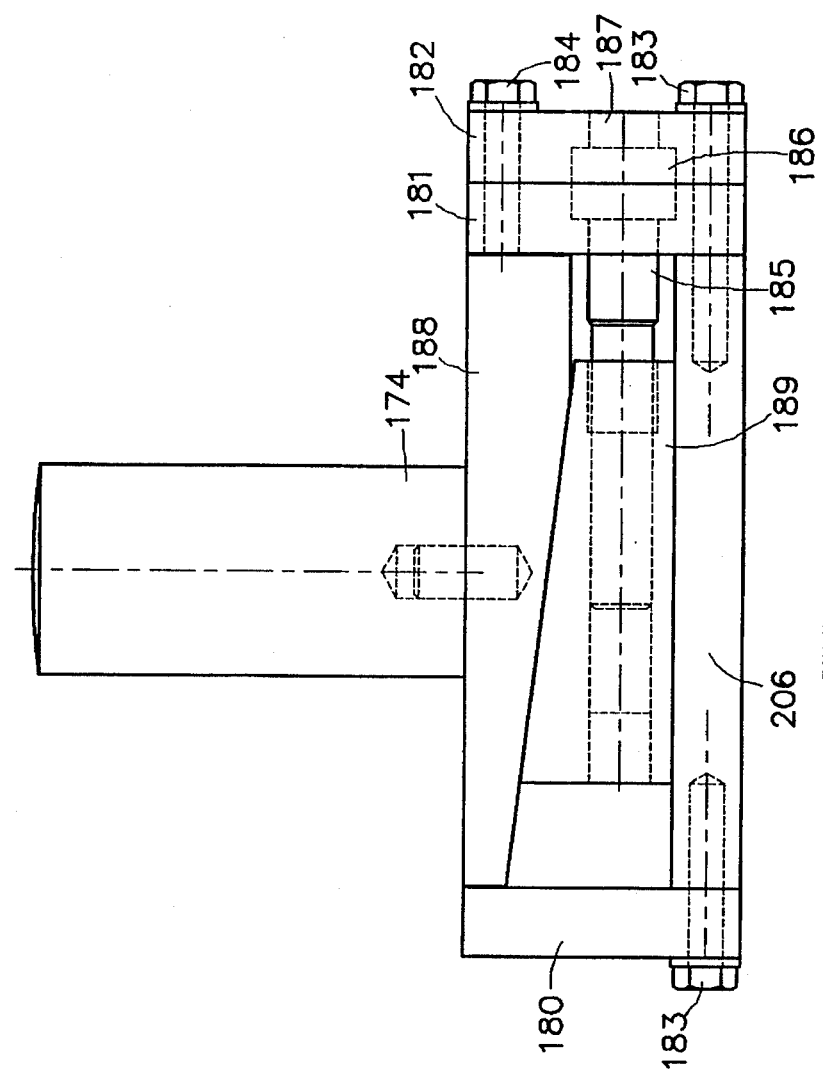
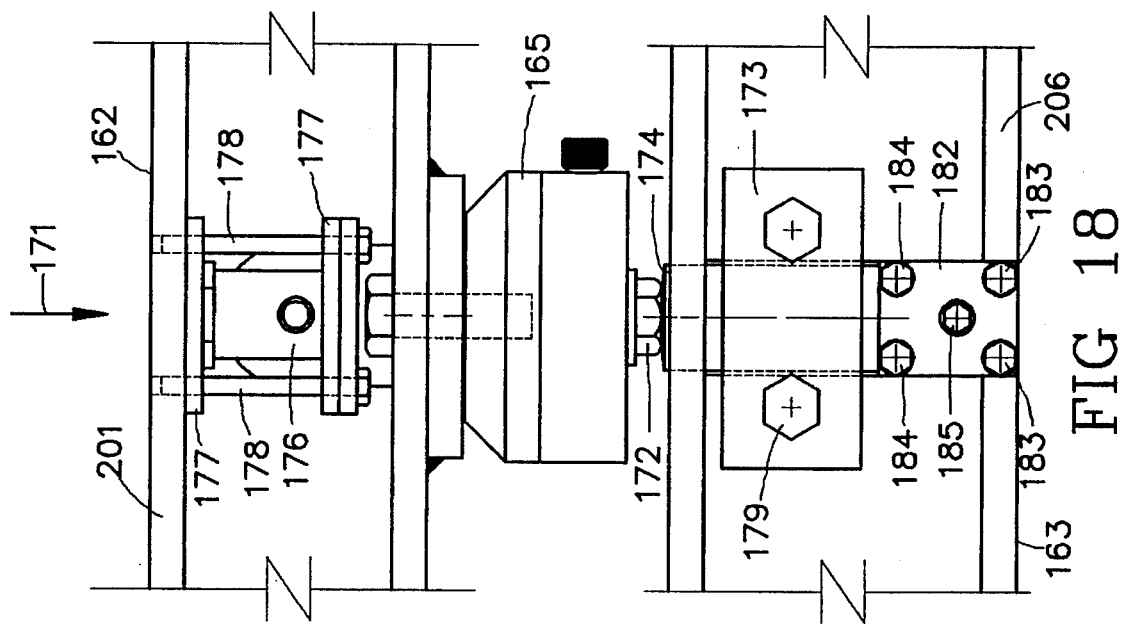

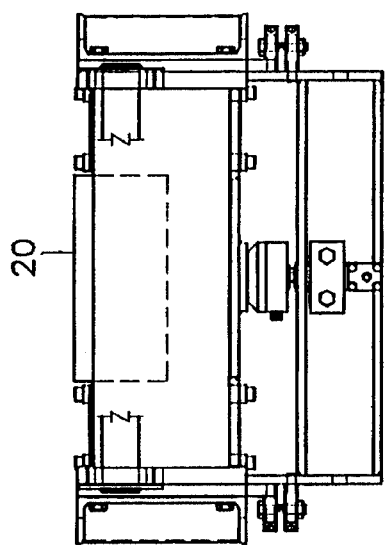
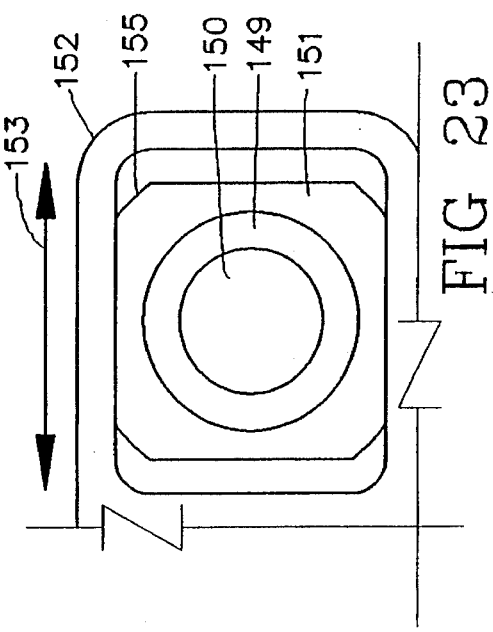
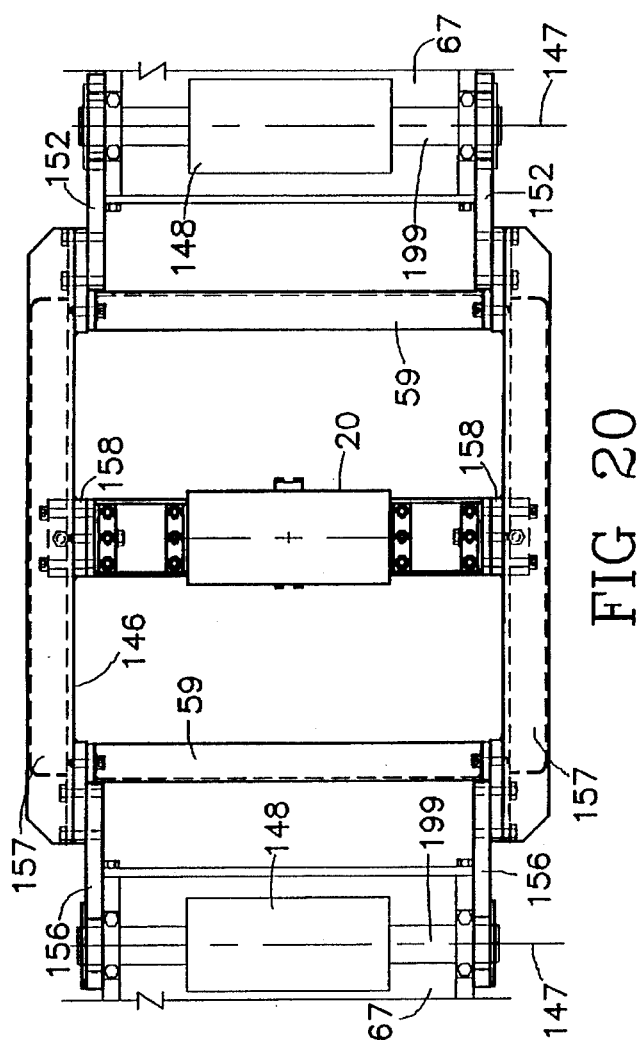
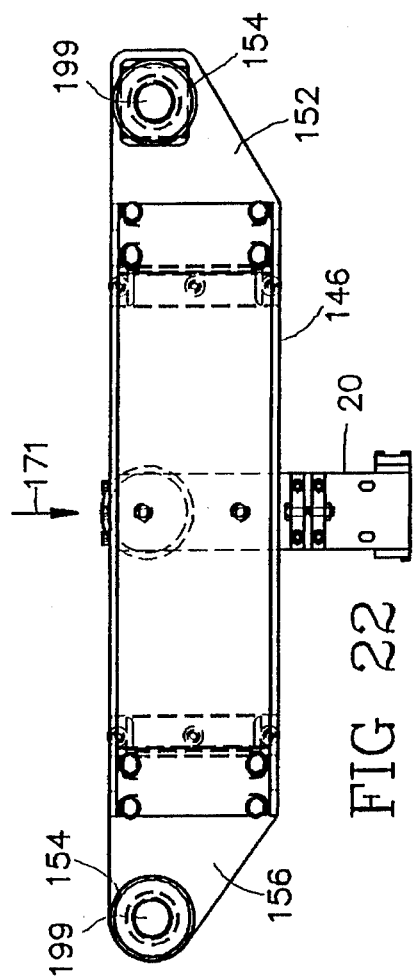

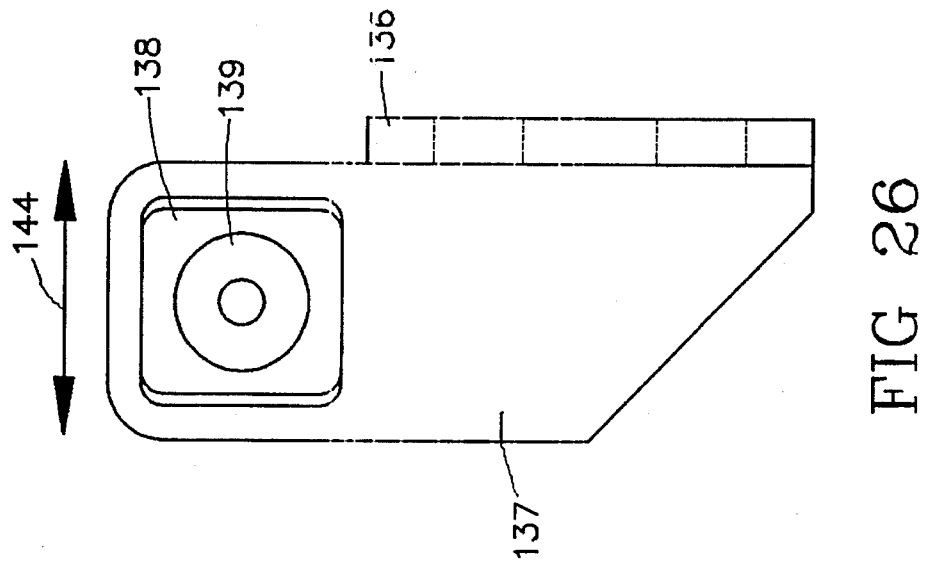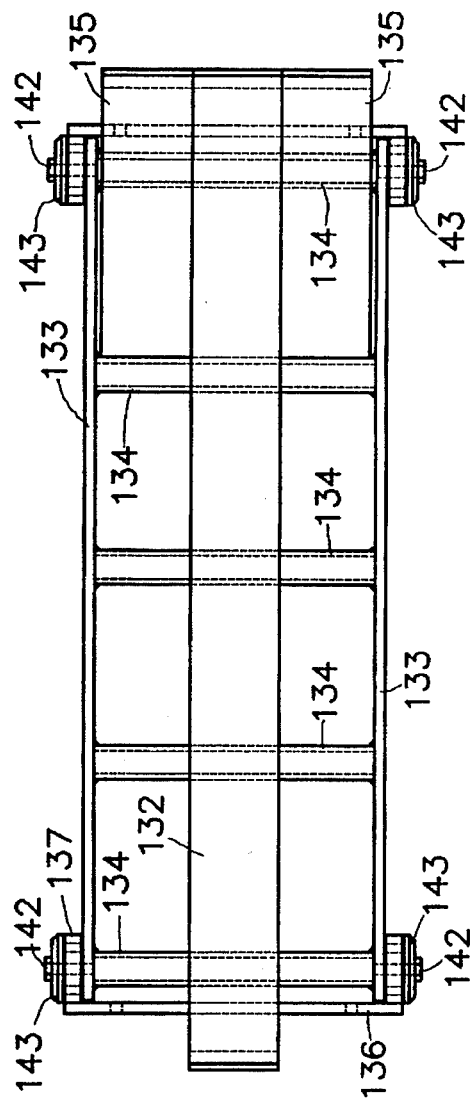

APPARATUS FOR TESTING LUMBER STIFFNESS

TECHNICAL FIELD

This invention relates to an improved apparatus for measuring stiffness of wood boards. The apparatus borrows heavily from apparatus described by Keller in U.S. Pat. No. 3,196,672, but introduces novel features and improvements.

BACKGROUND OF THE INVENTION

To use better the lumber produced by a modern mill, it is desirable to have some indication of the structural value of each board produced.

Means for Measuring Stiffness of Lumber, patented by Harold A. Keller in 1965, U.S. Pat. No. 3,196,672, has formed the basis for a machine, known as the CLT Continuous Lumber Tester (CLT), used commercially in production lines for the production of machine stress rated (MSR) lumber. The CLT is responsible for most of the production-line testing of lumber stiffness in North America and, as production speeds increase in other parts of the world, the CLT is increasingly being used there as well. The CLT non-destructively obtains measurements of bending stiffness, which it relates through lumber cross-section size and bending span length to the material property modulus of elasticity (E) for each wood board passing through the machine. Strength correlates with E sufficiently well that E is used as an indicator of strength as well as being important in its own right.

The CLT, positioned typically at the output of a high-speed planing unit, accepts lumber boards from the planer, bends each board by a fixed deflection, first downward in a first test span and then upward in a second test span, averages the forces required at each of the two test spans to eliminate effects of board weight and straightness deviations, then after signal processing, marks each board with an ink spray mark to indicate the E category.

The CLT is built on a framework to which are mounted three fixed clamp carriages spaced along the framework and bolted to it. Each fixed clamp carriage contains four rollers, two of which are 8.5 inches [215.9 mm] diameter and two of which are slightly smaller than 4.5 inches [114.3 mm] diameter. All six of the large (8.5 inch) clamp rollers, two in each of three fixed clamp carriages, are driven by two motors. Each motor drives three rollers via sprockets on the ends of the roller shells that are connected together for motive purposes by timing belts.

Three additional clamp carriages are movable with respect to the CLT framework. The motion of each of these movable clamp carriages is guided translationally in the vertical direction by slide bearings and by a rack and pinion assembly that together prevent any significant rotation of the movable clamp carriage about either a vertical axis or an axis parallel to the lumber flow. The number, size and arrangement of rollers in the movable clamp carriages are the same as in the fixed clamp carriages, except the movable clamp carriages are located on the opposite side of the lumber from the fixed clamp carriages.

Each movable clamp carriage is positioned so that its rollers press the lumber against rollers in a corresponding fixed clamp carriage. Force to lift and press the movable clamp carriages against the lumber and thence against the fixed clamp carriages is provided by air powered actuators, one for each movable clamp carriage.

Thus, in the CLT each of the fixed and movable clamp carriages contains two large and two small rollers. For all four clamp rollers in a clamp carriage to contact a lumber surface on a common plane, the small rollers have axes that are displaced from the large rollers in a direction perpendicular to the contacted lumber surface. In the CLT this displacement distance is two inches [50.8 mm]. With 8.5 inch [215.9 mm] and 4.5 inch [114.3 mm] diameters for the large and small rollers respectively, and the above displacement, the rollers would all be tangent to a common plane. This would be true for the rollers in each of the fixed clamp carriages on one side of the lumber and also for the opposed rollers in the corresponding movable clamp carriages on the other side of the lumber. However, machine manufacturing tolerances and discrepancies in thickness along a wood board would lead to situations where not all rollers contact the board on both sides simultaneously. Because only the two large rollers in each fixed clamp carriage are driven, there are conditions where contact of these drive rollers to the board surface and hence motive force for propelling the board through the machine would be lost.

To avoid losing motive force in the CLT, the small clamp rollers are reduced in size by a small amount to ensure roller contact with the wood board surface by the large driven rollers under all reasonable conditions. Although some clamping pressure at the small rollers is lost, this tradeoff is essential because of the serious consequences of measurement inaccuracy if the speed of the board is not maintained through the machine.

The three combinations of movable and fixed clamp carriages isolate two bending test sections from effects of forces external to the test sections. A total of 24 clamp rollers clamp lumber between the movable and fixed clamp carriages, control the position of the lumber at the ends of the two test sections and propel it through the machine. At the center of each test section, a load roller forces a fixed deflection of the lumber, and the force required to achieve this deflection is sensed by a strain gauge type load cell. The two test sections are similar, except that in one test section the lumber is bent in one direction, and in the other it is bent in the other direction. By delaying the force signal from the load cell in the first test section by the amount of time required for a point on a wood board to move from the first to the second test section, the two force signals from a common location on the board can be combined to form one-half their sum. The result, known as local E, is compensated for warp of the wood board.

Lumber enters the CLT through an infeed guide, recently modified with an airoperated mechanism to allow easier clearing of material jams. Each board is gripped between the rollers of fixed and movable clamp carriages and propelled into and through the machine by the large driven clamp rollers in the fixed clamp carriages.

Adjustable stop bolts attached to the movable clamp carriages limit the movement of the movable clamp carriages and establish the opening between rollers in the fixed and movable clamp carriages when lumber is not in the CLT. If stop bolts are set for too large an opening, the movable clamp roller carriages do not move enough to grip the lumber adequately against the fixed clamp carriages or to bend the lumber by the amount required to achieve accurate readings. In this case, motive force may be lost, and a reduction in grade yield will occur. When the stop bolts are set for too small an opening, the movable clamp carriages will be closer than they should be to the fixed clamp carriages when boards are not in the machine. This leads to more translational motion than desirable for the movable clamp carriages as boards enter and exit the machine, thus causing increased machine wear, but most importantly, measurement errors, i.e. inertial noise, due to the inertial effects of accelerating masses. Compensation for inertial noise has been introduced to the CLT E measurement process, and inertial noise compensation is disclosed in U.S. Pat. No. 4,991,446; but, it is better to minimize the motion and avoid introducing the inertial noise in the first place by careful stop bolt adjustment rather than to compensate for the inertial noise errors in the measurement once they have been introduced.

Steel guides (recently improved in the CLT), one located in the first test section and another in the second test section, guide the leading ends of boards smoothly in the direction of bending between the rollers of fixed and movable clamp carriages as the boards enter and exit the spaces between these pairs of carriages. These guides help reduce mechanical shock and vibration and thus improve measurement accuracy by reducing inertial noise.

Two opposed, longitudinal fences extend throughout the length of the CLT, forming a channel down the centerline of the CLT to control the position of wood boards laterally in a direction perpendicular to the direction of bending. These fences are pressed by air powered actuators in a direction toward the CLT longitudinal centerline against adjustable stops to accommodate lumber having different lumber widths.

In each test section, a load roller deflection assembly bends the lumber by a fixed amount. CLT load roller assemblies are comprised of two load roller halves on a shaft, a means by which the load roller can rock about a longitudinal axis of the machine to track twist in the surface of lumber traveling through the CLT, and a supporting structure by which it is mounted at one end with flange pivot bearings or, more recently, by flexure couplings (U.S. Pat. No. 4,932,267) to the CLT frame.

In the CLT, lumber is bent downward in the first test section and then upward in the second test section. In each test section, the force required for bending is measured by a load cell and force measuring system, and the upward and downward force measurements are averaged point-by-point along the length of the lumber to obtain "local E" as a function of position along the length. The force signal from the load cell in the first test section is delayed in an electronic data processing unit before averaging with the force signal from the second test section. The delay, equal to the amount of time required for lumber to travel from the first to the second test section, is required so that downward and upward forces are combined (averaged) at the same points along the lumber. This local E measurement is processed in the electronic data processing unit to obtain an average value "Average E" and a lowest value "Low-point E" over the length of the lumber. Average E and Low-point E are used in the United States and Canada to determine an E category and define an ink spray color mark that is applied automatically to the lumber. In some countries, only the Low-point E is used and in some countries spray marks identifying local E are applied along the length of the boards.

Photosensors detect the ends of the wood boards and thereby control timing of the Average E and Low-point E computational process as well as timing of E category determination and application of ink spray marks.

Three major features of the CLT retained by the present disclosure are: 1. two test sections and signal averaging to compensate the E measurement for warp of a board; 2. fixed-deflection force measurement (as opposed to fixed-force deflection measurement) to reduce errors in the measurement caused by inertial noise; and 3. multiple clamp roller supports at ends of test sections to isolate measurements from effects of external forces.

FEATURES AND ADVANTAGES OF THE PRESENT INVENTION WITH COMPARISON TO THE PRIOR ART

The above general overview of the CLT Continuous Lumber Tester describes the most advanced prior art for measuring lumber stiffness. Here, objectives of the present invention are listed along with discussion of how the present invention meets these objectives and resolves problems with the prior art.

OBJECTIVES OF THE PRESENT INVENTION

(a) Increase Structural Rigidity

Measurement error duct to inertial noise has been a continuing problem with the CLT. Various parts of the CLT apparatus have vibration modes in the frequency range of interest for measuring wood stiffness. By carefully mounting the CLT, reducing clearances of moving parts, signal filtering, and compensating for measurement errors caused by vibration, it is possible to achieve excellent performance. However, as a practical matter, force signals from CLTs can have significant components of inertially caused noise in them, this noise being attributed to mechanical vibration.

The apparatus of the present invention has been carefully configured so that vibration modes have frequencies well above the frequency content of force signals obtained while measuring lumber. With this separation of frequency content between noise and information, high frequency noise signals can be electrically filtered out without losing information about the lumber stiffness. Resulting signals have reduced noise when compared with the CLT so that the filter low-pass cutoff frequency can be increased, and measurement signals with higher frequency content can be passed than for the CLT. Thus, the apparatus can obtain higher quality local E information about each wood board tested.

(b) Simplify Manufacturing and Maintenance Requirements of the Multiple Clamp Rollers The twelve large clamp rollers in the CLT are friction-attached to shafts, and the shafts are mounted through roller bearings to a clamp carriage frame. Friction-locking devices are used to attach rollers to shafts, and they can be tightened in a way to minimize the roller runout. Tightening is done selectively with multiple screws, all the while checking the runout with a dial indicator. This laborious process successfully reduces the runout to acceptable levels.

In the CLT, roller bearings that support the roller shafts fit into bored holes in the clamp carriage frame. The holes in the clamp carriage frame must fit the bearings closely. Too much clearance allows too much radial motion of the rollers, which leads to even more clearance as the bearing outer races wear in the holes of the clamp carriage frame. Too little clearance leads to large thrust loads on the bearings during assembly as they are tightened to the roller shafts via threaded tapered sleeves. Thrust loads on these bearings lead to early bearing failures. These issues apply equally well to the twelve small clamp rollers, except that the small clamp rollers and shafts are one-piece weldments that depend on accurate machining for acceptable runout and do not require a laborious process of tightening them to shafts.

Although this arrangement functions well if every step of the manufacturing and assembly process is done properly, the process is time consuming and expensive; further, it must be done by well-trained individuals.

In the preferred embodiment of the present invention, the clamp rollers rotate about their shafts, and each shaft is fixed to its clamp carriage frame by screwed-on caps. Machining to achieve this mounting arrangement is accomplished efficiently, the problem of concentrically attaching rollers to shafts by careful assembly is avoided, and the rollers themselves are simply steel tubes with bored holes in their ends for bearings to be mounted. No welding is required on either shafts or rollers, as opposed to the CLT, where welding is required in the construction of both large and small clamp rollers.

The CLT uses 24 clamp rollers and two load rollers, the set comprising three basically different types and having three different diameters. The present preferred embodiment uses 18 clamp rollers and two load rollers, the set comprising one basic type and one diameter. All rollers on the present machine are configured so the roller shells rotate on bearings about stationary shafts. Standard sealed bearings, which require no lubrication, are used instead of the shielded bearings of the CLT, which require regular greasing. The manufacturing and assembly process of the rollers for the present invention inherently results in concentricity of better than 0.002 inch [0.05 mm] TIR (Total Indicated Runout); whereas, in the CLT this standard can be met only with great care.

(c) Improve Motive Rorce on the Lumber

In the CLT each of three fixed and three movable clamp carriages has two large and two small clamp rollers. In the preferred embodiment of the present invention, all rollers are the same diameter. Whereas the CLT uses four rollers in each clamp carriage, the present invention uses three. Where only the two large clamp rollers in each fixed clamp carriage of the CLT are driven, all three clamp rollers in each of the fixed clamp carriages of the present invention are driven. To ensure that motive force is applied consistently to lumber in the CLT, the small clamp rollers in each fixed and movable clamp carriage are located and sized to miss the plane of contact defined by the lines where the large clamp rollers of the carriage contact the lumber. If manufacturing accuracy in the CLT were perfectly held exactly to the nominal values, large rollers would compress the lumber surface by about 0.0075 inch [0.19 mm] before the small rollers contact the lumber. Because the large rollers compress the lumber surface, the small rollers make contact and perform their task of providing clamping pressure. However, this is not equivalent to, nor as good as, the clamping that results if all rollers meet the plane of the lumber surface substantially simultaneously as in the present invention. The present invention does not require any of the rollers to be set back from the lumber surface, because all clamp rollers in the fixed clamp carriages are driven, and motive force is consistently applied to the lumber.

(d) Reduce Unintended Bending Moments by Clamp Rollers on Uniform Straight Lumber In the Keller patent and in the CLT implementation of it, clamp rollers meet the lumber on opposite sides of the lumber. However, in both the Keller patent and in the CLT implementation of it, the clamp rollers that move in translation against the lumber to clamp it against opposing rollers, move in a direction perpendicular to the longitudinal axis of the apparatus. This will satisfy the condition of the rollers being directly opposed across the lumber from each other for just one thickness of lumber. The problem in the CLT is that the fixed clamp carriages are mounted at a slight angle to the CLT machine framework; whereas, the motion of the movable clamp carriages is perpendicular to the longitudinal axis of the apparatus instead of along a direction at a slight angle to this perpendicular. In the Keller patent, clamp rollers in movable clamp carriages at both ends of each test section are illustrated as being mounted on a common frame element. Thus, they cannot move in a direction to be directly opposite the corresponding rollers in fixed clamp carriages except for one lumber thickness. For any thickness of lumber other than the one where the clamp rollers are directly opposed, an error moment will be created due to the misalignment from the directly opposed condition. This error moment is a function of clamping pressure as well as the amount of misalignment.

In the preferred embodiment of the present disclosure, the problem is resolved by organizing the clamp rollers into three clamp units, each of which has a fixed clamp carriage with three clamp rollers and a movable clamp carriage with three clamp rollers. Each complete clamp unit is mounted in the frame of the apparatus at a small angle known as the clamp angle for the clamp unit. Because each movable clamp carriage moves within guides that are part of the clamp unit, the orientation of the movable clamp carriage motion relative to the fixed clamp carriage does not change either with lumber thickness or with clamp angle. Thus, corresponding clamp rollers in fixed and movable clamp carriages are directly opposed across the lumber from one another for all thicknesses of wood boards.

(e) Simplify the Load Roller Assembly and its Mounting

Each of the two load rollers in the CLT is mounted on a support beam that is rotatably supported at its one end by a frame, and, at its other end, by a force sensing load cell. Spring force is required in one of the two test sections to counter the effect of gravity and hold the support beam against the load cell when no lumber is in the machine. In early CLT machines, roller bearings were used to support one end of the support beam, and a separate spring was used to counter the effect of gravity. In recent CLT machines, the functions of both the roller bearings and the spring have been replaced with flexure couplings (U.S. Pat. No. 4,932, 267). The load roller applies force to a wood board, and a component of that force is sensed by the force sensing load cell. The support of each load roller to its support beam is by two trunnion bearings having a common axis in a longitudinal direction of the machine and two spindle bearings having a common axis in a transverse direction. Rotation of the load roller about the spindle bearings is caused by lumber moving past the roller. Limited oscillatory rotation about the trunnion bearings is due to twist in the lumber and the load roller following these deviations from straightness. This leads to a requirement in the CLT that the lumber must travel down the center of the machine. Otherwise, the rotational degree of freedom about the trunnion bearings would affect the deflection amount and hence the force measured.

In the present disclosure, the oscillatory motion of the load roller is eliminated, and a suspension system is specified that allows the same force to be measured regardless of whether the lumber is centered in the machine or passes through it near one side. The support beam is eliminated, and the load roller suspension system is configured so that the force sensing load cell reads substantially all the force applied by the wood board to the load roller, instead of just a component of it.

(f) Provide a Simple and Convenient Means of Adjusting Movable Carriage Stops It has been learned through years of experience with the CLT that adjustment of the mechanical stops, limiting how closely the movable clamp carriages may approach the fixed clamp carriages when lumber is not in the machine, is critical. The required clearances in the CLT are difficult to inspect and awkward to adjust. In the present specification, a design is disclosed that allows these clearances to be inspected and adjusted easily.

(g) Reduce the Possibility of Slippage of Material Traveling Through the Machine This disclosure teaches a drive arrangement whereby all the rollers in the fixed clamp carriages can be driven, rather than just half of them as with the CLT. Not only does this reduce the possibility of lumber slippage in the present invention, but it allows all clamp roller-to-wood line contacts to be coplanar for rollers in each clamp carriage, thereby improving the clamped end supporting conditions for the lumber tested.

(h) Reduce Binding of Movable Clamp Carriages in their Motion for Clamping Lumber In the CLT, a bridge frame in the second test section is rotatably supported between the movable clamp carriages at the ends of the test section. The purpose of the bridge frame is to support the load roller deflection means for that test section. Although the movable clamp carriages in the CLT move on parallel tracks in a direction perpendicular to the framework longitudinal axis, the carriages do not necessarily move in unison during the clamping process. Because the bridge frame ties them together, if one carriage moves before the other, a binding action will result. The solution in the CLT is to increase the longitudinal clearance of guides that both allow vertical motion and restrict longitudinal motion of the movable clamp carriages. However, the increased longitudinal clearance also increases longitudinal motion of the movable clamp carriages, worsens the moment problem, mentioned in (d) above, and makes these moments more unpredictable.

The present disclosure teaches that a translational degree of freedom built into the attachment points at one end of a bridge frame will eliminate the binding problem. Because the movable clamp carriages at the ends of the bridge frame of the present disclosure do not move along parallel tracks, it is essential that this degree of freedom be provided.

(i) Eliminate Need to Adjust Board Guides as a Function of Lumber Thickness

For each of the two test sections, the CLT uses steel guides to guide, in the direction of bending, wood boards smoothly out from between clamp rollers at the upstream end of the test section and into the space between clamp rollers at the downstream end of the test section. In both test sections the guides are referenced and attached to the apparatus main frame. For the second test section, the one having the bridge frame, the guide is fixed to the main frame, and its adjustment is independent of wood board thickness.

In the first test section, if the guide is fixed to the main frame as it is in the CLT, an adjustment as a function of board thickness is required for smooth operation. A study of the Keller patent reveals that the corresponding guide in that patent was referenced to CLT rollers in a movable clamp carriage and therefore would not require adjustment as a function of board thickness. The CLT design did not follow the teachings of Keller in this regard.

The present disclosure teaches that the board guide in the test section without the bridge frame should be referenced to the movable clamp carriages as Keller teaches, but to make this work properly without causing the movable clamp carriages to bind, particularly when these carriages move on off-parallel tracks as the present disclosure teaches they should, an additional translational degree of freedom must be provided. This translational degree of freedom can occur anywhere along the guide, but most conveniently at the supports on one end. This disclosure teaches that some resilience at each of the attachment points of these board guides is desirable to help reduce shock and vibration in the apparatus as wood boards pass through, thus reducing inertial noise errors in the measurement.

(i) Eliminate Lateral Fences

Keller teaches the requirement to keep the board on the centerline of the machine as it passes through and recommends use of a line bar and slightly canted rollers for this purpose. This is an important teaching of Keller because it has been observed that if a wood board is not approximately centered in the CLT, significant measurement errors can occur. The CLT uses longitudinal fences through the machine with air powered actuators to hold the fences against adjustable stops. The purpose of these fences is to keep the lumber on the machine longitudinal center-line. The present disclosure teaches that the requirement for centerline feed and passage is unnecessary, provided the deflection means are properly constructed so that the same forces are measured regardless of where the wood board passes over them. By eliminating the requirement for the longitudinal fences, the apparatus of the present disclosure does not have a limit on how thin the boards may be. While the CLT is used successfully to test 1.375 inch [35 mm] thick lumber, it is unlikely that it would be useful for thicknesses much less than that.

In reference to using a line bar and canted rollers as suggested by Keller to achieve centering, it has been observed that errors arising from friction increase in the CLT when the lumber is allowed to run against the fences. For this and the reasons cited above, it is desirable to eliminate the need for fences.

BRIEF DESCRIPTION OF THE DRAWINGS

FIG. 3 is a plan view of the mechanical apparatus with main frame.

FIG. 4 is a side elevation view of the mechanical apparatus with main frame.

FIG. 8 is an end elevation view of the mechanical apparatus showing specifically the first board guide.

FIG. 9 is a side elevation view of the mechanical apparatus showing specifically the first board guide.

FIG. 11 is a plan view of a movable clamp carriage showing clamp roller shells, shafts and mounting of second clamp rollers to the clamp carriage frame.

FIG. 12 is a side elevation view of the items in FIG. 11.

FIG. 13 is an end elevation view of the items in FIG. 11.

FIG. 14 is a plan view of a lower guard.

FIG. 15 is a side elevation view of a lower guard.

FIG. 18 is an enlarged view of the load cell adjustment mechanism, load cell and its mounting, and accelerometer and its mounting in the structure of FIG. 17.

FIG. 19 is an enlarged side cut-away view of the load cell adjustment mechanism in the structure of FIG. 17.

FIG. 20 is a plan view of a bridge frame, illustrating also parts of the movable clamp carriages in the second and third clamp units, second test section reference rollers, and second deflection means.

FIG. 21 is an end elevation view of the structure of FIG. 20.

FIG. 22 is a side elevation view of the structure of FIG. 20.

FIG. 23 is an expanded view of the bearing arrangement of the bridge frame mounting shown at the right of FIG. 22, with large diameter washer removed to illustrate better the bearing arrangement and showing the direction in which this arrangement allows translational movement of the bridge frame.

FIG. 24 is a plan view of a second or third board guide.

FIG. 25 is a side elevation view of the board guide of FIG. 24.

FIG. 26 is a side elevation view showing for the board guide of FIG. 24, a board guide end plate, board guide supports, resilient interface, hub, and the direction in which this arrangement allows translational movement of the board guide.

DESCRIPTION OF THE PREFERRED EMBODIMENT

Figure 1:
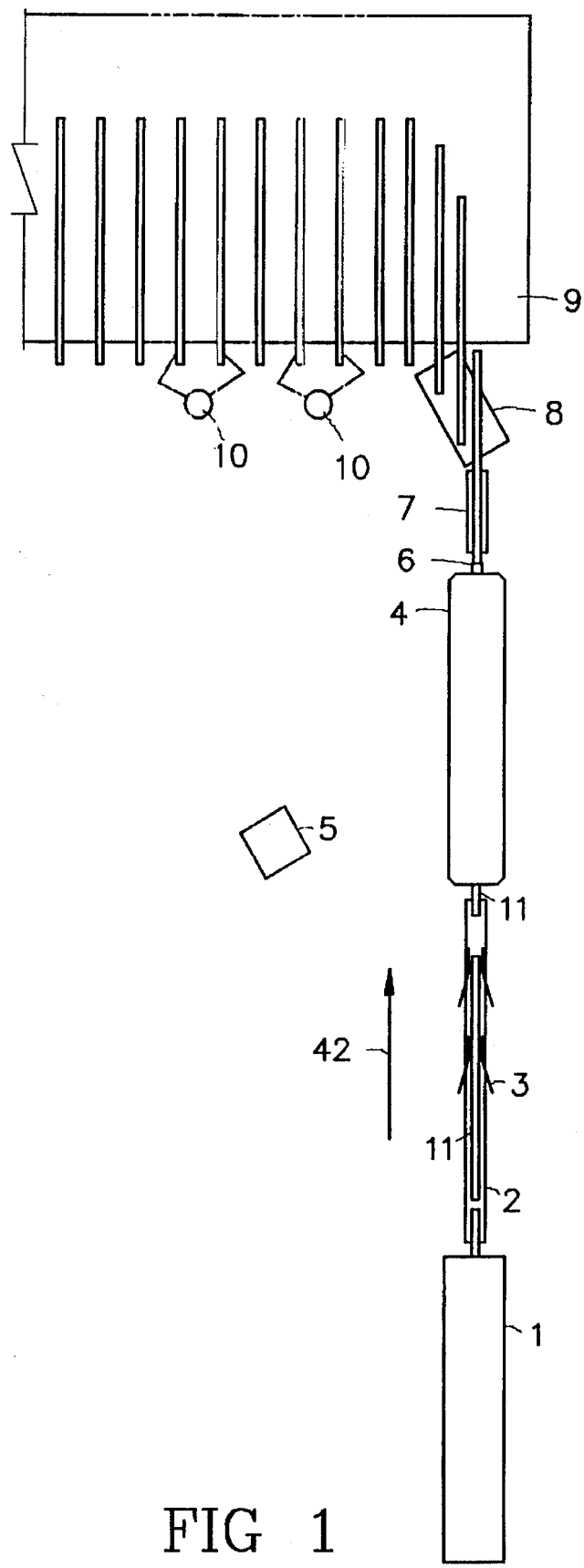
FIG. 1 is a plan view of the apparatus in a typical enviromnent showing its use.

The preferred embodiment of the invention is illustrated in the accompanying drawings. It is to be understood that this apparatus is merely one example of a physical embodiment that can be utilized in the present invention. The machine shown in the drawings is not intended to limit or restrict the scope of the invention except as that scope is defined in the claims that follow.

Referring to FIG. 1, planer 1 surfaces boards 11 to size and puts them on conveyor belt 2. Conveyor belt 2 is aligned with guide apparatus 3 to direct the boards in direction 42 into mechanical apparatus 4 of the present invention. As will become clear from the description to follow, centering of the boards is not essential for accurate measurements, as it is with prior art. The measurement sequence, signal processing and control of outputs are handled in an electronic unit 5, which is part of the apparatus of the present invention. After boards pass through the apparatus, they are marked by a spray marking means 6 that identifies the boards or areas on the boards according to their modulus of elasticity (E). Although not essential, usually the spray marking means 6 is mounted directly to the apparatus 4 at its outfeed end. Signals to control the spray marking means are provided by outputs from the electronic unit 5. The spray marking nozzle of U.S. Pat. No. 5,074,244 has been found to be particularly effective for spray marking. After the boards are marked according to their measured E, they are shown in FIG. 1 traveling on conveyor belt 7 to slowdown belt 8, which is arranged so as to slow the boards and place them on landing table 9 in position to move transversely past human graders 10 who determine the grade of each board. The spray marks applied to the boards provide information about the structural quality of the boards that the human graders would not have otherwise. This system allows human graders to use E as well as visual characteristics to make a better judgment about the proper grade, and allows the boards to be sorted into grades known in North America as machine stress rated lumber grades. Many other configurations are possible, the one represented in FIG. 1 being one of the simplest.

Figure 2:
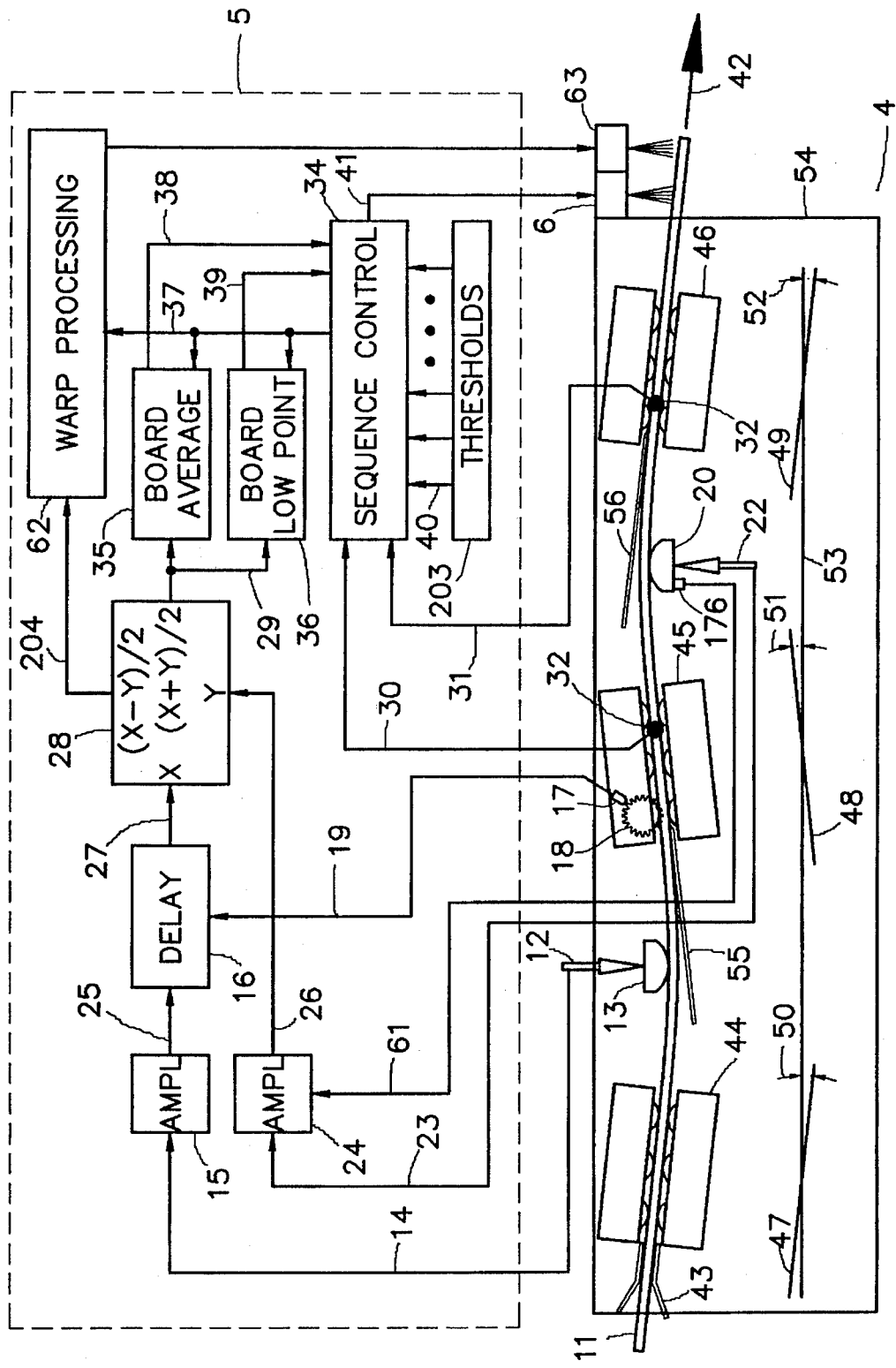
FIG. 2 is an elevation mechanical schematic view with an electric schematic diagram to provide an overview of the apparatus and its function.

Referring now to FIG. 2, a mechanical and electrical schematic view of the apparatus 4 and electronic unit 5 is illustrated. The mechanical schematic should be interpreted as a side elevation view and will be useful in identifying the layout and positioning of the major components. Wood boards 11 enter the apparatus 4 moving longitudinally with respect to their length. In the apparatus, each board is bent first downward in a first test section and then upward in a second test section. A first force 12 required to bend the board downward by a specified amount in the first test section is sensed by a first force sensor. The first force sensor is located within a first deflection means 13 in the first test section. The sensed force signal is a function of time, time being related by the board speed to position along the board. The first force signal is sent over wire cable 14 to a first amplifier 15 and thence to delay module 16. Amplifier 15 amplifies and scales the first force signal according to cross-section size of the wood board, so that the amplifier output 25 is a first E signal, that is, it is a voltage that can be read as having units of modulus of elasticity, e.g. in psi [Pascals].

Pulses generated from a magnetic pickup 17 adjacent the rotating teeth of a steel sprocket 18, where the passage of each tooth represents a known distance of travel by the wood board, are transmitted over wire cable 19 to control the amount of delay in the delay module 16. The delay module delays the first E signal by an amount of time equal to the time required for a point on the board 11 to travel from a point adjacent to deflection means 13 to a corresponding point adjacent a second deflection means 20 in a second test section. The amount of delay time required is determined automatically in the present invention, as it is similarly in the present implementation of the prior art CLT Continuous Lumber Tester, by counting pulses from magnetic pickup 17. Sprocket 18 is attached to a roller that is in intimate pressure contact with the wood board, as will become evident from further discussion; hence, distance traveled by the board is related directly to sprocket rotation and the number of teeth passing by magnetic pickup 17. The result is a delayed first E signal 27.

In the second test section, a second force 22 required to bend the board upward by a specified amount is sensed by a second force sensor that is located within a second deflection means 20. The second force signal as a function of time is sent via wire cable 23 to a second amplifier 24 that amplifies and scales the second force signal so that output 26 is a second E signal.

It has been found that accelerometer 176 is useful for providing signal over cable 61 to the second amplifier 24 for the purpose of measuring small accelerations at the second deflection means and correcting the resulting measurement error due to inertial noise that these accelerations cause in the second force signal. Correction is accomplished by adding a compensating component to the second force signal that is out of phase with the acceleration caused noise error on the second force signal. This inertial compensation concept is described in more detail in U.S. Pat. No. 4,991,446. Although processing is the same, location of the accelerometer in this preferred embodiment is more straightforward than that described in the mentioned prior art, because of the improved deflection means of this disclosure.

Summing module 28 computes one-half the sum of the delayed first E signal 27 and the second E signal 26 to obtain the local E signal 29. By this means of combining bending measurements in two opposed directions, the result is substantially independent of deviations from straightness in the lumber.

Signals 30 and 31 from photosensors 32 are processed in a sequence control module 34 to control the timing of a board average module 35 and a board low point module 36. Signal 37 lets these modules know when a board is present. Board average module 35 averages the local E signal 29 during the time both photosensors 32 are blocked by the same wood board; the output is Average E. Board low point module 36 determines the lowest local E signal 29 during the time both photosensors are blocked by the same wood board; the output is Low Point E.

The board Average E value 38 and Low Point E value 39 are compared in the sequence control module 34 with multiple thresholds 40 set into the system at 203 by an operator. The result of the comparisons is an E category that controls spray marking means 6 by connection through wire cable 41. Details of this process are well known by those skilled in the art as presently practiced in the CLT Continuous Lumber Tester.

A new feature obtains another local measure, in addition to local E, called local warp 204, relating to deviation from straightness, by computing one-half the sum of the delayed first E signal 27 and the negative of the second E signal 26. The local warp measure 204 can be obtained simultaneously with the local E measure 29 in summing module 28. Independent warp processing 62 can be used to direct a separate spray marking means 63 as shown in FIG. 2, or local warp 204 can be combined with local E in a common processing unit, not shown, to control just the one spray marking means 6 according to criteria involving both E and warp.

Now, concentrating on the mechanical apparatus schematic 4 in FIG. 2, board 11 enters the apparatus moving from left to right in a direction indicated by arrow 42. Lead end board position is controlled both horizontally and vertically by a first board guide 43. First, second and third clamp units 44–46, having clamp reference planes 47–49, are spaced longitudinally along an elongated main frame 54 having frame reference plane 53. Main frame 54 is shown in outline form only in FIG. 2. The clamp reference planes are perpendicular to the plane of the elevation view in FIG. 2 and hence intersect this view along the lines indicated. As can be seen from FIG. 2, the clamp reference planes intersect the frame reference plane at clamp angles 50–52.

Each of the three clamp units consists of sets of opposed rollers that clamp the wood board and provide motive force for urging the board in direction 42 through the apparatus.

In the center of the first test section a first deflection means 13 forces a selected first deflection downward on the wood board, and in the center of the second test section a second deflection means 20 forces a selected second deflection upward on the wood board. A second board guide 55 guides the board into the second clamp unit 45, and a third board guide 56 guides the board into the third clamp unit 46. Although FIG. 2 does not show it, details of the second and third board guide to be described will make clear that they also guide the trailing ends of wood boards out of the first and second clamp units.

The first and second clamp units isolate the first test section so that forces applied to the wood board outside the first test section do not appreciably affect the measured force 12. Similarly, the second and third clamp units isolate the second test section. The extents of the first and second test sections are the spaces between their isolating clamp units. Thus, the clamp units define the test sections.

For clarity, the clamp angles 50–52 in FIG. 2 are greatly exaggerated from those used in the preferred embodiment. Clamp angle 50 is a small negative angle, clamp angle 51 is a small positive angle equal to the negative of clamp angle 50, and clamp angle 52 is equal to clamp angle 50. These clamp angles and the first and second deflections are selected to be in correspondence with each other, so that the moment exerted on a straight, uniform wood board by the clamp units is zero. Such a straight, uniform board would exert the same force on the deflection means if the ends of the board engage all the clamp rollers in the two clamp units defining the test section or just those rollers nearest the deflection means. The condition for this to hold is:

$$\text{Slope}=3* \text{ Deflection/Span} \tag{1}$$

where Slope is the tangent of the clamp angle, Deflection is the amount of deflection forced by the deflection means, and Span is the length of the test span between clamp units. In the preferred embodiment described here, wood boards can be considered to be 1.5 inch [38.1 mm] thick, and Slope= $5/256$, Deflection=$5/16$ inch [7.938 mm] and Span=48 inch [1219 mm].

Figure 28:
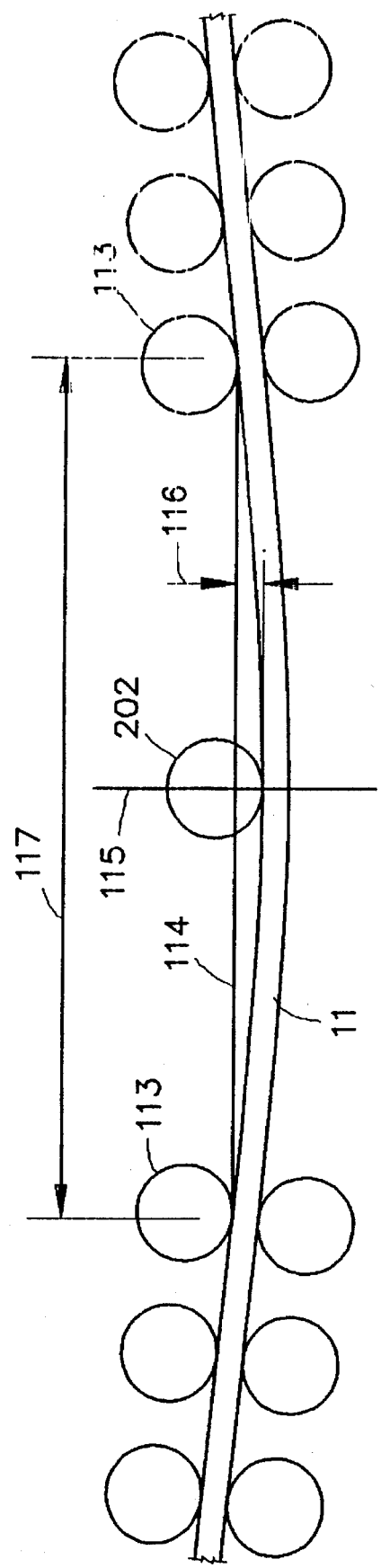
FIG. 28 is an expanded simplified view of the apparatus of FIG. 2 in the area of the first test section showing reference planes and the amount of deflection.

It is useful to examine more closely the region around either the first or second test section. The area around the first test section is shown expanded and simplified in FIG. 28. Here, the clamp rollers adjacent the first test section in the first and second clamp units, and on the same side of the wood board as the first deflection means, are defined as the first test section reference rollers 113. A first test section reference plane 114 is defined as the plane that is tangent to the first test section reference rollers as shown. The first deflection means 13, which has a deflection reference plane 115 defining its orientation, is located so that the deflection reference plane 115 is perpendicular to the first test section reference plane 114, parallel to the clamp roller axes and located substantially in the center of the first test section as shown in FIG. 28. These reference planes are shown as lines in FIG. 28 because, in this side elevation view, the reference planes intersect the plane of the paper at right angles along the lines shown. The first deflection means is shown as a roller 202 in FIG. 28, although a skid plate might be used. The deflection distance used in Equation (1) above is the distance 116 illustrated in FIG. 28 measured from the first test section reference plane 114 to the position of the wood board forced by the first deflection means. Span is the distance 117 illustrated in FIG. 28. For the second test span, reference rollers and deflection means are on the other side of the wood board, and bending is up instead of down; otherwise, reference rollers, reference planes, deflection and span distances are defined similarly for the second test section as for the first.

Referring to FIG. 3 and FIG. 4, which are plan and elevation views of apparatus 4, the apparatus of the preferred embodiment can be seen with some details shown. These figures show the apparatus without safety guards and with many details still obscured. However, parts are shown in proper relation with one another, and the figures will be useful when taken in conjunction with other figures.

Main frame 54 consists of ½ inch [12.7 mm] wall rectangular tubular steel elements 57 combined into a rigid weldment. Additionally, removable 1×3 inch [25.4×76.2 mm] steel struts 58 and cross channel members 59 are fastened rigidly to the frame weldment. So constructed, and further braced by clamp unit attachments to the frame, the frame vibration modes have frequencies well above measured signal frequencies of interest. Additional frame rigidity as well as damping can be introduced by filling the tubular elements with concrete or other suitable filler for this purpose. In the frame of the preferred embodiment, vibration modes have frequencies above 100 Hz.

First, second and third clamp units 44–46 and first and second deflection means 13 and 20 are shown in both FIG. 3 and FIG. 4. First, second and third board guides 43, 55 and 56 are illustrated in FIG. 4, but not in FIG. 3.

Figure 5:
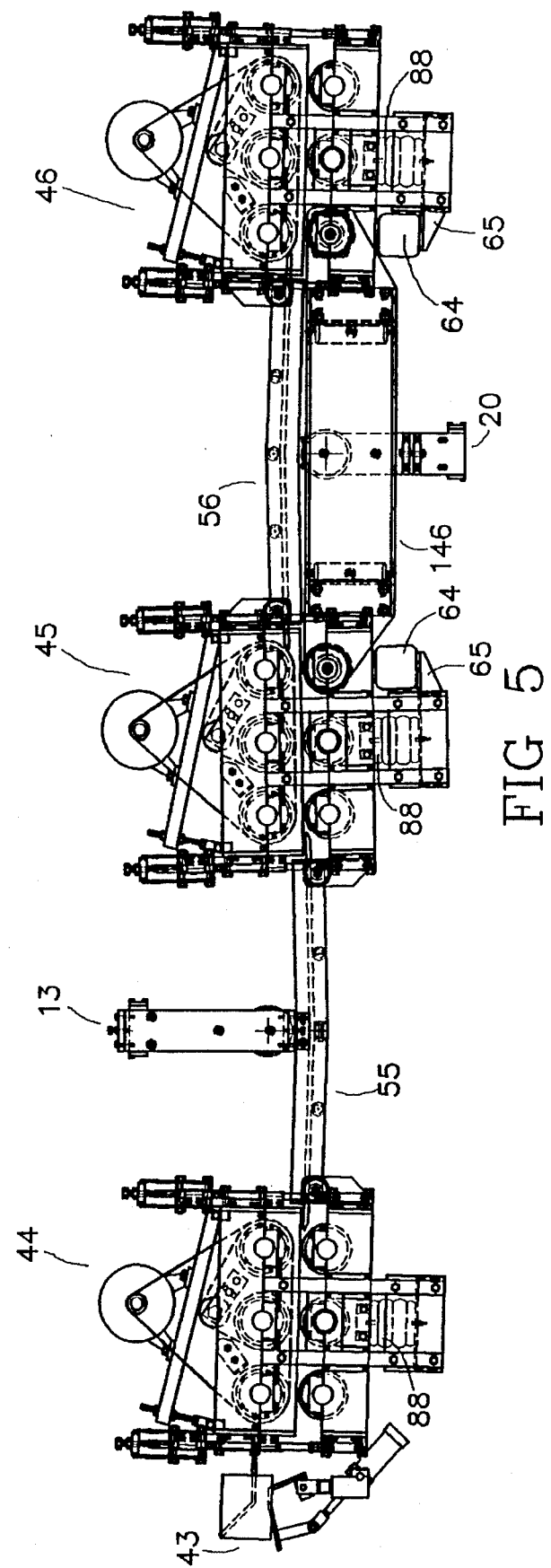
FIG. 5 is a side elevation view of the mechanical apparatus with main frame removed.

First, second and third board guides 43, 55 and 56, first, second and third clamp units 44–46, and first and second deflection means 13 and 20 are illustrated in FIG. 5, which is a view similar to FIG. 4, but without the main frame.

Figure 6:
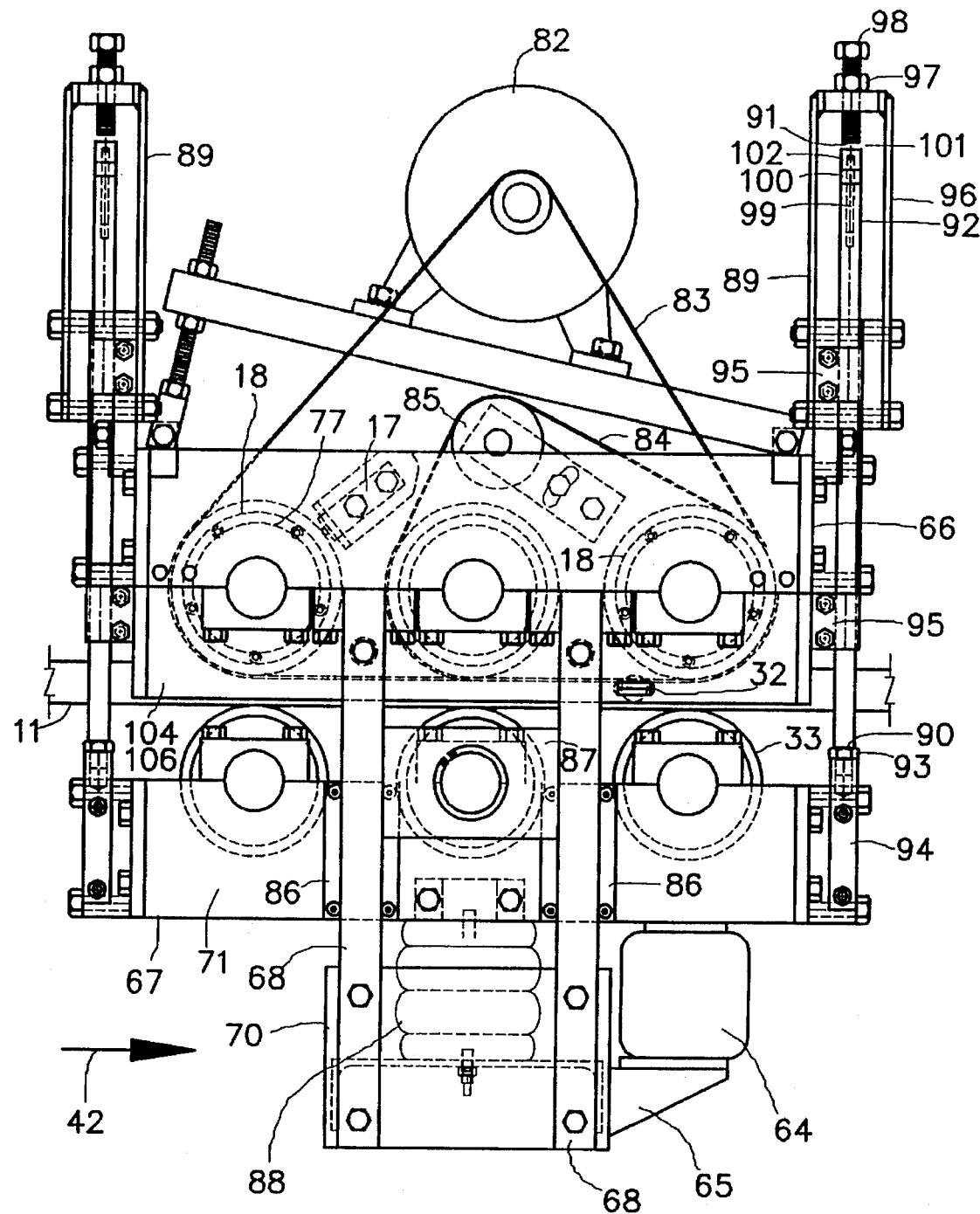
FIG. 6 is a side elevation view of a clamp unit showing its movable clamp carriage in the up position clamping a wood board against clamp rollers in a fixed clamp carriage.

FIG. 6 is a side elevation view of a clamp unit that could be any one of the three clamp units 44–46, except that the direction 42 of wood board motion through the clamp unit and the location of auxiliary actuator 64 and its mounting 65 on the downstream end make it the second clamp unit 45. The third clamp unit would have the auxiliary actuator and mounting on the upstream instead of the downstream end. The first clamp unit has neither an auxiliary actuator nor a mounting for it. These differences can be seen in FIG. 5. The auxiliary actuators are provided on the points shown on the second and third clamp units to support the extra weight of deflection means 20 and a bridge frame 146 used to mount deflection means 20 in the second test section.

Still referring to FIG. 6, each clamp unit consists of a fixed clamp carriage 66 and a movable clamp carriage 67. The fixed and movable clamp carriages are much the same, each having three clamp rollers and a carriage frame. The clamp rollers in fixed clamp carriages are referred to as first clamp rollers, and the clamp rollers in movable clamp carriages are referred to as second clamp rollers. The fixed clamp carriage 66, steel guides 68 and clamp base 70 are fastened rigidly together, thereby comprising a clamp unit frame.

The clamp reference plane of the clamp unit is parallel to a plane that is tangent to the first clamp rollers in the fixed clamp carriage. In FIG. 6, the movable clamp carriage is shown in the up position against a wood board 11. Thus, except for compression of the wood fibers perpendicular to grain and irregularities in the wood surface geometry, the lines of contact of the first clamp rollers with the upper surface of the wood board define a plane parallel to the clamp reference plane. Similarly, the lines of contact of the second clamp rollers with the lower surface of the wood board define a plane parallel to the clamp reference plane. This assumes that the wood board is clamped, and the clamped faces of the wood board are parallel. While it is recognized that lines of contact of clamp rollers to a wood board surface are actually areas of contact due to contact pressure and compression of wood fibers, the compression usually is not large, and, for descriptive purposes, the board is treated as being incompressible, with board-to-roller contacts being straight lines.

Figure 7:
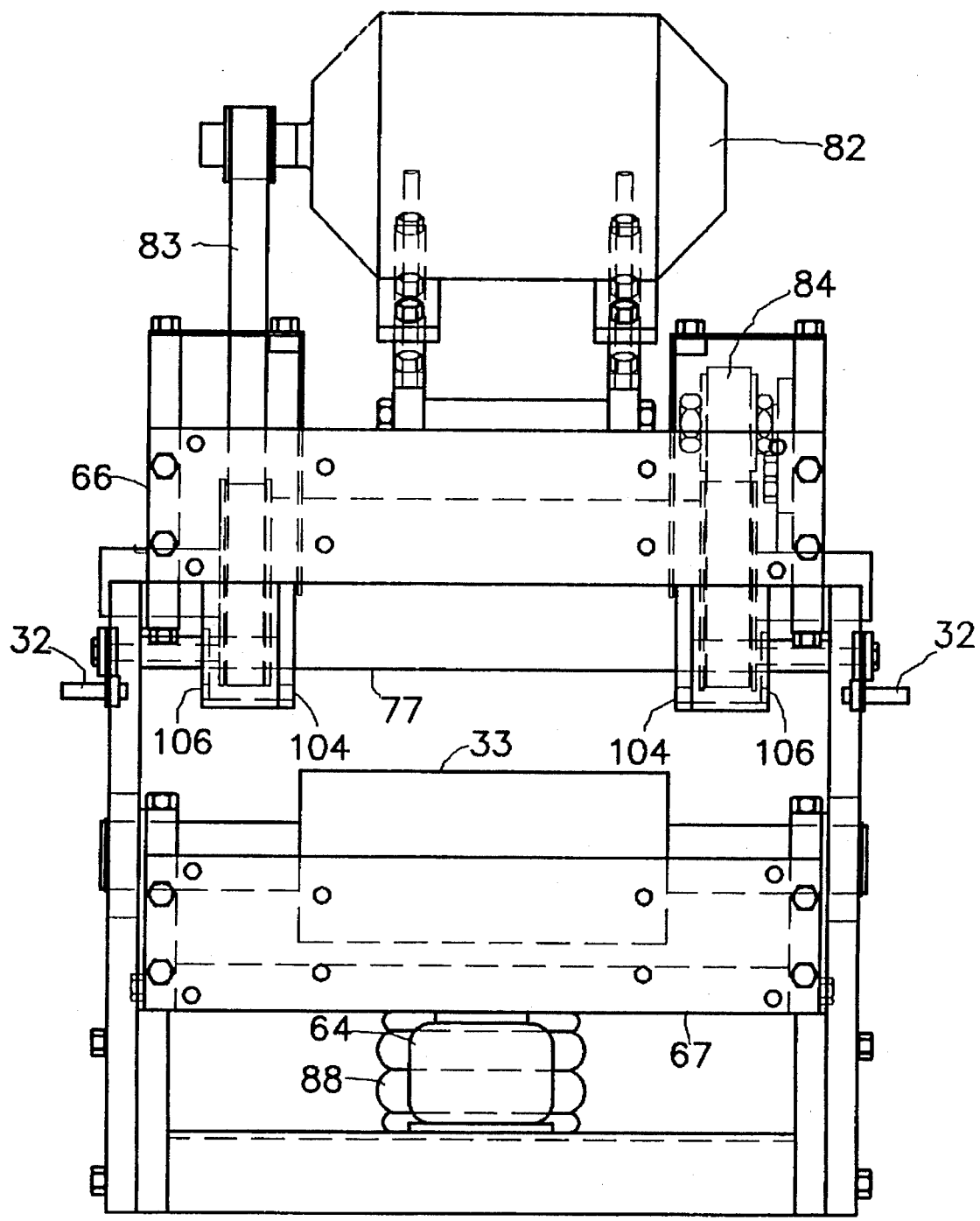
FIG. 7 is an end elevation view of the clamp unit of FIG. 6, but showing the movable clamp carriage in the down position, stop assemblies removed and wood board not present.
Figure 27:
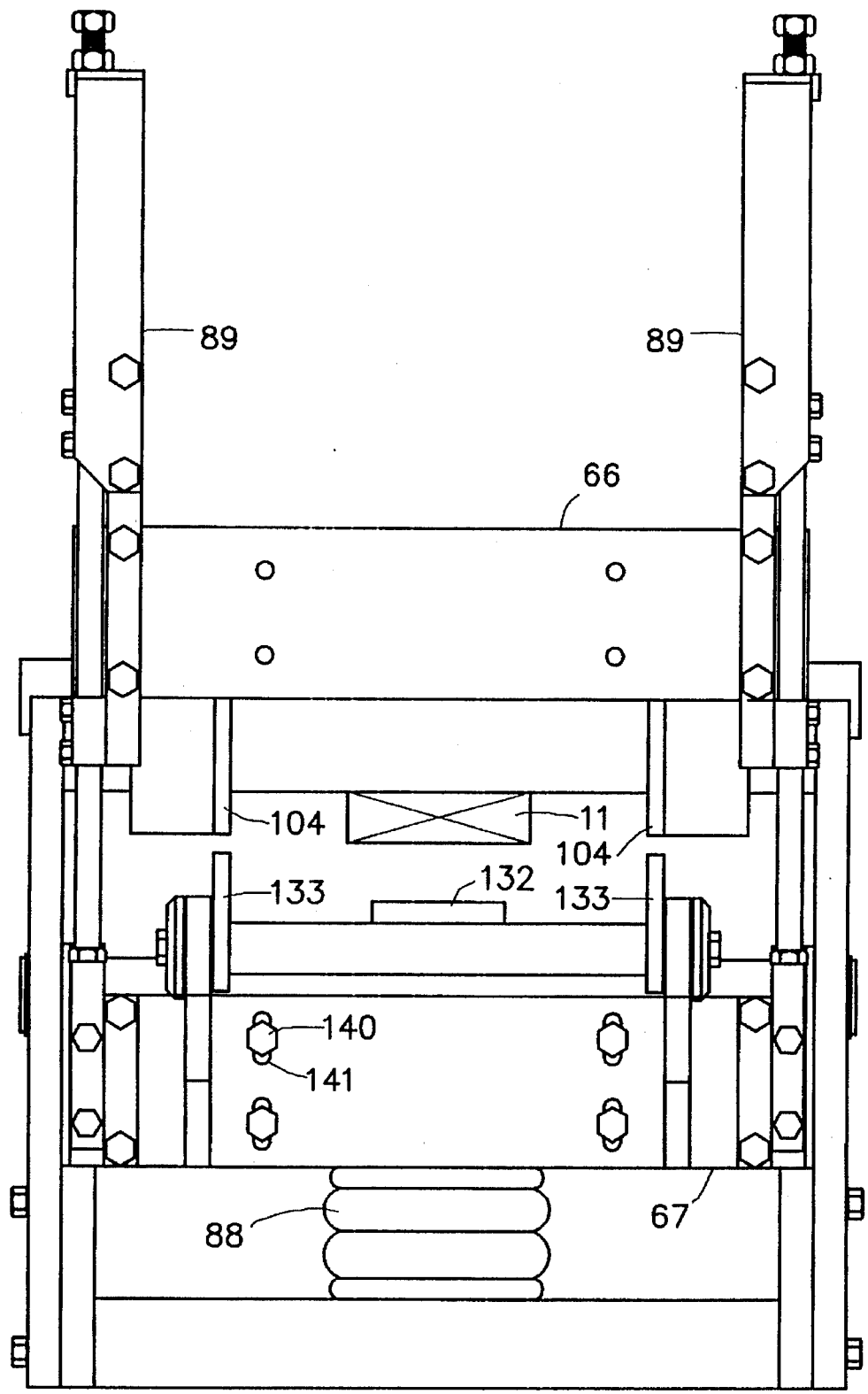
FIG. 27 is an end elevation view looking upstream at the first clamp unit showing the second board guide and stops installed, but with some other components absent.

First and second clamp units are elevation views from the end looking upstream in FIG. 27 and in FIG. 7 respectively. In each of these views, some components have been removed to avoid obscuring other details. In both figures, the movable clamp carriage is shown in the down position, although in FIG. 27 a wood board 11 is shown where it would be when clamped.

Three views, FIGS. 11–13, of a movable clamp carriage 67 show a clamp carriage frame 76, shafts 75 and 199 and second clamp roller shells 33. Each clamp carriage frame consists of steel side plates 71 bolted to steel end plates 72. Side plates are fitted with steel caps 73 bolted together at their edges. Holes with diameter 2.125 inch [53.98 mm] are bored with centers on the interfaces between side plates and caps and spaced 8 inches [203.2 mm] along the side plates. Prior to boring, shims 0.010 inch [0.254 mm] thick are sandwiched between caps and side plates, and cap screws 74 are tightened firmly. By this means, shafts can be clamped in position to the side plates by using the caps without the shims. Alternatively, boring can be accomplished without the shims and 0.010 inch [0.254 mm] milled from the interfacing cap surface after boring. Shafts 75 and 199 having diameter 2.1875 inch [55.56 mm] are turned to 2.1654 inch [55.00 mm] in the regions where bearings are mounted and 2.125 inch [53.98 mm] diameter where they are clamped by the caps to the side plates. Shafts 199 are longer than shaft 75.

Now referring also to FIG. 6, a long shaft 199 is used for the clamp roller in the center of each movable clamp carriage to support, at each end, plastic guide blocks 87, which move within the constraints of steel guides 68. A long shaft 199 is used also for a clamp roller shaft at one end of each of the second and third movable clamp carriages as a supporting interface for a bridge frame to be described. Clamp roller shells 33 are steel tubing finished to 5.480 inch [139.2 mm] diameter with bearing housing recesses machined in the ends. These recesses are sized to accept sealed bearings such as Part Number 311NPP available from the Torrington Company in Torrington, Conn.

Each fixed clamp carriage is similar to the movable clamp carriage of FIGS. 11–13. The major difference is that first clamp roller shells in a fixed clamp carriage have sprockets on one or both ends (see FIG. 10) for drive purposes. The center first clamp roller has a long shaft to assist in attaching the clamp unit to the apparatus main frame by means to be described later. Referring to FIG. 6, motor 82 drives timing belt 83, sprockets 18 and both first clamp rollers at the ends of the carriage in counter-clockwise rotation. At the other end of the down-stream first clamp roller (right-most first clamp roller in FIG. 6), another sprocket is mounted to drive, via timing belt 84 and idler sprocket 85, the center first clamp roller, which has a sprocket on its end nearest the idler sprocket. The purpose of idler sprocket 85 is to keep proper tension on timing belt 84.

Figure 10:
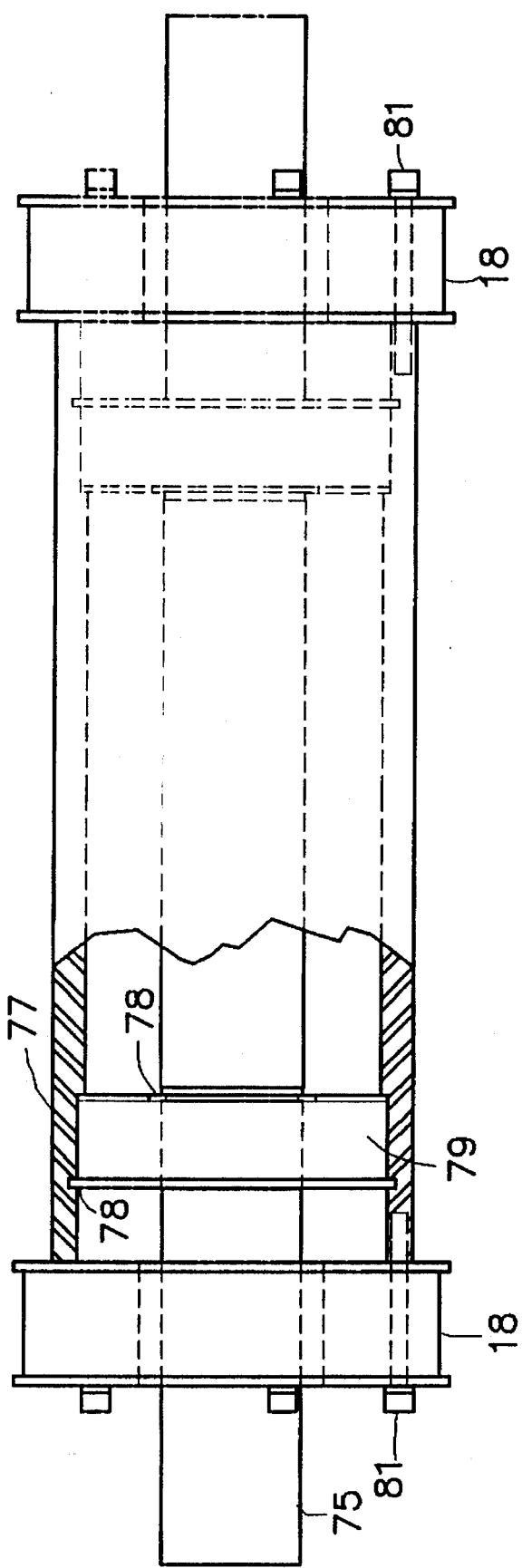
FIG. 10 is a partial cut-away view of a first clamp roller.
Figure 16:
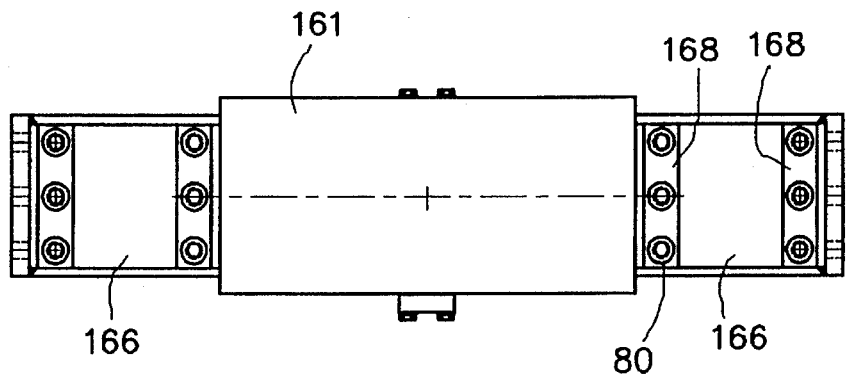
FIG. 16 is a plan view of the second deflection means.
Figure 17:
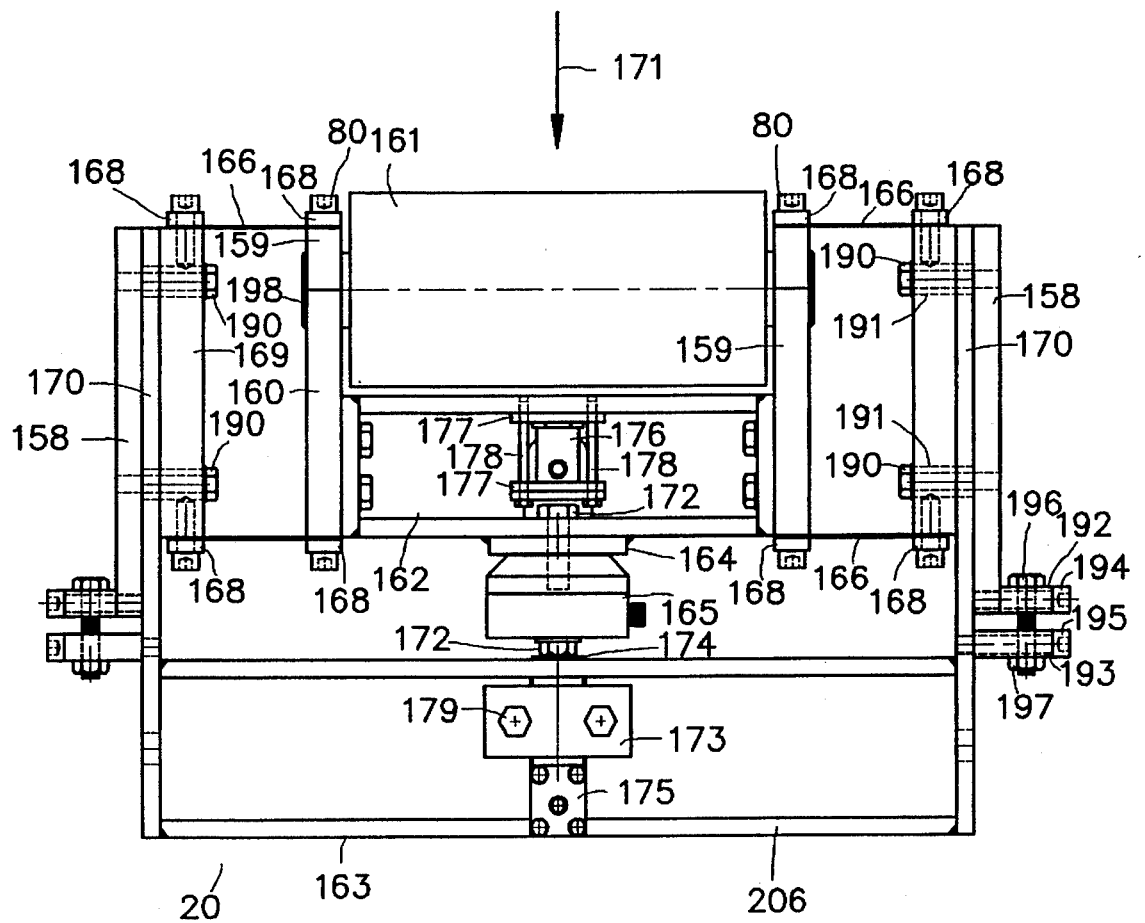
FIG. 17 is an end elevation view of the second deflection means.

A typical first clamp roller shell, bearing and shaft assembly is shown in FIG. 10. In FIG. 10, four snap rings 78 retain two bearings 79 within roller shell 77 and in position along shaft 75. The assembly of FIG. 10 has timing belt sprockets 18, for example Part Number 8M-63S available from the Gates Rubber Company in Denver Colo., mounted on its ends by screws 81 that fasten into the ends of the roller shell, thereby holding the sprockets firmly in place. The sprockets have recessed bores in them to position them on center over the roller shell. The sprockets identify the clamp roller of FIG. 10 as one of the clamp rollers for a fixed clamp carriage; that is, the roller is a first clamp roller. However, except for the lengths of the roller shells and shafts and presence of the sprockets, the other details of shafts, bearings and roller shells are the same as for the second clamp rollers in movable clamp carriages.

The advantages of clamp roller construction as in FIG. 10 and mounting as in FIGS. 11–13 are the tolerances that can be maintained and the ease of achieving them. Accuracy in machining of roller shells and shafts is essential, but no welding is required on these parts. Location of the shafts along side plates 71 can be accomplished efficiently and precisely. Once machining is accomplished, assembly is simple.

Referring again to FIG. 6, timing belts 83 and 84 are more difficult to replace than if they were used to drive the shafts instead of the rollers directly. However, replacement has been eased by the method of clamping shafts with caps 73. And, it is recommended that timing belts be oversized to reduce the need to change the belts. The preferred embodiment uses 36 mm wide Polychain belts available from the Gates Rubber Company.

Each movable clamp carriage 67 is mounted within a clamp unit frame as illustrated in FIG. 6. Two plastic bearing pads 86 fastened to each movable clamp carriage frame side plate 71 provide bearing surfaces and close fitting of the movable clamp carriage against steel guides 68 in the lateral direction (perpendicular to the plane of FIG. 6), thereby preventing motion of the movable clamp carriage in directions parallel to the clamp roller axes. Plastic slide bearing blocks 87, one mounted on the center roller shaft of the movable clamp carriage on the side facing the viewer in FIG. 6 and one similarly on the opposite side (not shown), are closely fitted within the steel guides 68 and provide bearing surfaces against the steel guides in directions both parallel to the clamp reference plane and perpendicular to the clamp roller axes, thereby preventing translation of the movable clamp carriage in those directions. By this supporting arrangement, translation of the movable carriage is allowed in directions perpendicular to the clamp reference plane of the clamp unit, and rotation of the movable clamp carriage is allowed about an axis parallel to the clamp rollers but not about axes orthogonal to the clamp roller axes.

Air actuator 88, e.g. Part No. Y1-2B9-257 available from Goodyear Tire and Rubber Company in Akron Ohio, is used to force second clamp rollers of the movable clamp carriage up against a wood board 11 and clamp it against opposing first clamp rollers in the fixed clamp carriage.

There are two primary advantages in organizing fixed and movable clamp carriages together into a common clamp unit as described. First, the movable clamp carriage is, by design, controlled by the steel guides 68, bearing pads 86 and bearing blocks 87 to move in directions so that second clamp rollers in the movable clamp carriage are directly opposed across the wood board from corresponding first clamp rollers in the fixed clamp carriage for any thickness of wood board and for any clamp angles chosen. In the prior art, first and second clamp rollers on opposite sides of a wood board are directly opposed for only one board thickness for each clamp angle selected. Second, the whole clamp unit can be treated as an assembly, thereby simplifying repair or replacement. In the prior art, fixed and movable clamp carriages are not combined into common clamp units. For example, disassembly of the CLT for repair and reassembly is a laborious process involving disassembling rollers from shafts and taking these parts out of the machine individually and then reversing the process on reassembly.

Referring to FIG. 6 and FIG. 27, stop assemblies 89 are illustrated. There are four of these stop assemblies on each clamp unit, one at each of the four corners of the clamp unit. In the elevation views of FIG. 6 and FIG. 27, two of these assemblies are hidden behind the ones in view. The stops are intended to arrest upward motion of the movable clamp carriage when no wood board is present. Each stop assembly consists of a fixed reference 90, an adjustable reference 91 and a steel push rod transfer means 92 connecting the two references.

In this implementation, the fixed reference is fastened to the movable clamp carriage and has a hard surfaced flat wear face machined in the head of a hard machine screw 93, the screw being fastened into an attachment block 94, which is itself fastened to the movable clamp carriage 67. The push rod 92 is made from ¾ inch [19.1 mm] diameter stress-proof steel shafting and is guided within linear bearing supports 95, which are fastened to the fixed clamp carriage. The linear bearing supports are fabricated from aluminum blocks with close fitting holes bored to allow the push rod to pass through and allow longitudinal motion only. The adjustable reference 91 is a flat surface machined on the end of a machine screw 98 with extended threads. The screw 98 is threaded through a stop frame 96 that is fastened to fixed clamp carriage 66. A lock nut 97 fixes an adjustment once it is made.

With this stop arrangement, the movable clamp carriage moves up by air pressure applied to actuator 88 until upward motion is arrested either by pressure against the wood board 11 or by contact of the fixed reference wear faces 93 against the push rods 92 and thence by the push rods against the adjustable references 91.

In FIG. 6 a clearance 101 is shown between the top of each push rod and the adjustable reference. This clearance exists because a wood board is clamped in the clamp unit. It has been discovered that the amount of clearance is important for best accuracy of measurement. The clearance controls how much motion the movable clamp carriage undergoes as wood boards enter and exit the clamp unit on passage through the apparatus. If the clearance is too little, the boards are not clamped firmly and motive force is lost. In that case, the local E signal is not developed properly as one-half the sum of the delayed signal from the first test section and the signal from the second test section, and, in severe cases, jam-ups can occur. Also, full bending deflection in the test spans is not achieved. If the clearance is too much, then excessive movement of the movable clamp carriages leads to inertially caused noise in the signals. It has been discovered that clearances in the range 0.015–0.020 inch [0.381–0.508 mm] are about right depending on size of the wood boards. If the thickness of the wood boards tested is very consistent, then the stop clearances can be set even more closely. If the wood board thickness is inconsistent, greater clearance may be required.

The advantage of the stop assemblies as disclosed here is that the observed clearances and adjustments are transferred via the push rods 92 up to the top of the machine, where they can be inspected and adjusted easily. An additional feature of each push rod 92 is a removable hard end 102 with concentric pin 99 that extends down into the main part of the push rod. This allows a spacer 100 to be sandwiched between the hard push rod end and the main part of the push rod. The purpose is to allow rapid adjustment of the push rod reference when changing from one board thickness to another, for example from 35 mm to 45 mm, or vice versa, as is frequently done in some parts of the world. Spacers for specific thicknesses of wood boards can be fabricated easily. This arrangement also allows the spacer 100 to be fabricated of resilient material for some situations where that is desirable for reduction of measurement error due to inertial noise. In particular, this can be valuable where the board thickness is not controlled as consistently as it should be.

Lower guards 104, shown in plan and elevation views in FIGS. 6, 14 and 15 and which are made of ½ inch [12.7 mm] thick steel, protect the timing belts 83 and 84 from wood boards striking them and serve as longitudinal guides for the wood boards in the region of the clamp units. The lower guards have holes 107 machined in them to allow photosensors 32 mounted on opposite sides of the machine to look through the machine, including guards, and detect presence or absence of a wood board. Bosses 105 allow the lower guards to be mounted to the clamp frame via an intermediate external guard 106 (see FIGS. 6 and 7) used to protect personnel from the timing belts. From FIGS. 6 and 7, but assuming the movable clamp carriage 67 is in the up position in FIG. 7 instead of down as shown, it will be seen that first clamp roller shells 77, lower guards 104 and second clamp roller shells 33, establish a longitudinal channel in each clamp unit through which each wood board must go.

Figure 29:
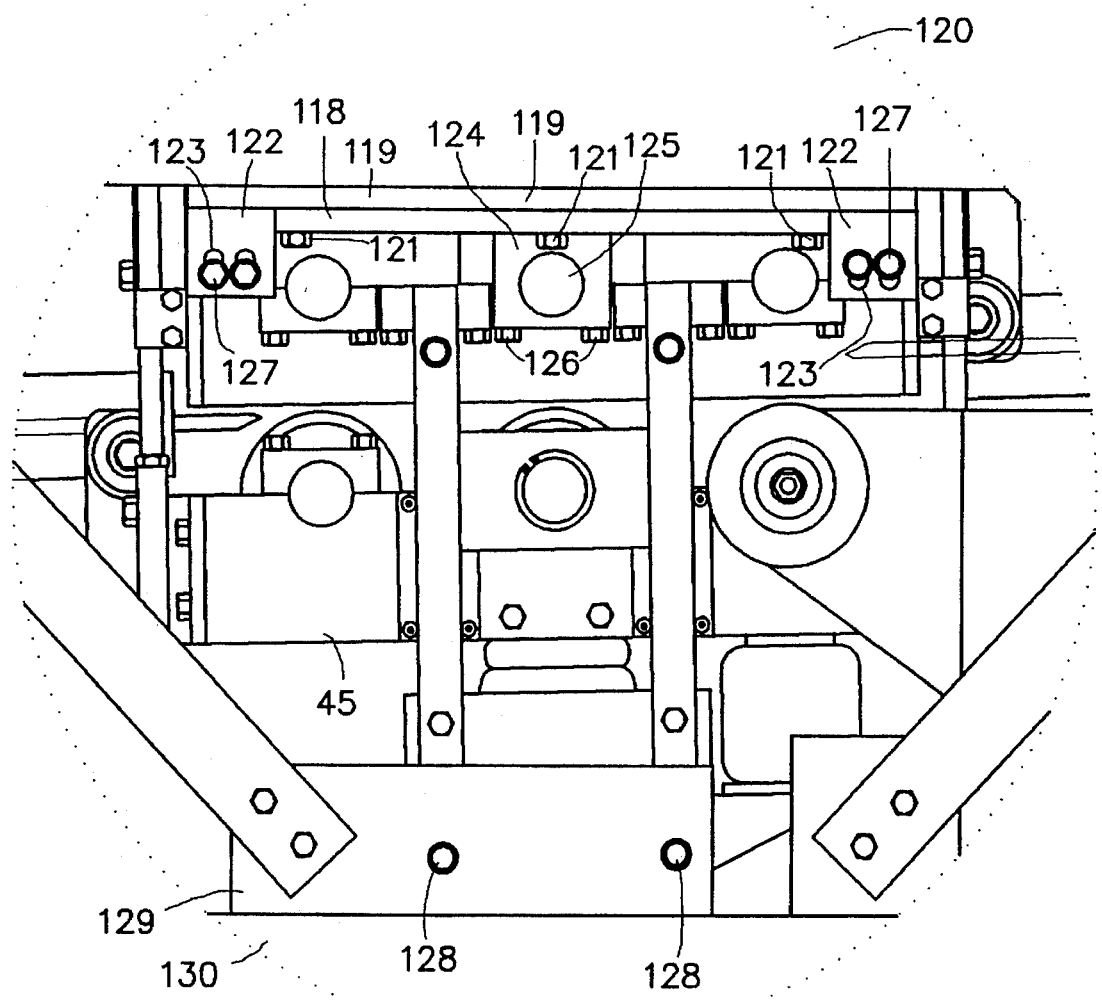
FIG. 29 is an expanded view of FIG. 4 in the region of the second clamp unit and shows the mounting of one side of the clamp unit to the frame.

Referring to FIG. 29 for an expanded side elevation view of the second clamp unit and the means for mounting one side of it to the frame, plate 118 is fastened by screws 121 to plate 119, which is itself welded to main frame upper tube element 120. Ears 122 with elongated attachment holes 123 are welded to plate 118. During assembly, the entire clamp unit 45 is lowered into the frame, and pivot block 124 is fitted over first clamp roller shaft 125, which is longer than the other first clamp roller shafts, and held to plate 118 by screws 126, which can be screwed in or out to adjust for a desired elevation of the clamp unit. The clamp unit is pivoted about shaft 125 to achieve the desired clamp angle 51 illustrated in FIG. 2. When the clamp angle and elevation of the clamp unit are achieved, screws 127 and 128 are tightened, thereby anchoring the clamp unit to the main frame. Screws 128 fasten the clamp unit to plate 129, which is welded to main frame lower tube element 130. The holes in plate 129 are enlarged to allow motion of the shanks of the screws 128 for clamp angle adjustment of the clamp unit before the screws are tightened. Large washers, not shown in FIG. 29, are used under the screw heads of screws 128. The other side of the clamp unit and the other clamp units are attached similarly.

FIGS. 8–9 show in detail a first board guide 43, through which lumber enters the apparatus and is directed into the first clamp unit 44. This guide comprises an immovable upper element 108 referenced to the first clamp unit fixed clamp carriage and fastened to the machine frame 54, and a lower element 109 that is movable through the action of an air cylinder 110. Additionally, immovable angled side plates 111 are welded to upper element 108. The first board guide makes the alignment of infeed apparatus for guiding wood boards into the machine less critical.

Referring to the side elevation views of FIGS. 5 and 25, second and third board guides 55 and 56 cause a wood board to deflect upward and enter the space between clamp rollers in the second clamp unit 45 and then to deflect downward and enter the space between clamp rollers in the third clamp unit 46. The second and third board guides are identically constructed, but the second board guide 55 is fastened to the movable clamp carriage in the first clamp unit 44 at the upstream end of the guide, and to the movable clamp carriage in the second clamp unit 45 at the downstream end of the guide. The third board guide 56 is inverted about a horizontal plane when compared to the second board guide. The third board guide 55 is fastened at its upstream end to the fixed clamp carriage in the second clamp unit 45 and at its downstream end to the fixed clamp carriage in the third clamp unit 46.

From FIGS. 24–26, the second and third board guides are seen to have a gentle V shape and to be comprised of a guide plate 132, edges 133, cross tubes 134 and guide wings 135, all welded into a steel guide weldment 145. Additionally, each board guide comprises guide end plate 136, guide supports 137, resilient interfaces 138 and hubs 139 at each end for mounting purposes. The V shape allows these board guides to guide the trailing ends of wood boards out of the clamp units to which they are attached at their upstream ends as well as guide the leading ends of the boards into the clamp units at their downstream ends. Guide plate 132 which, for the preferred embodiment, is ½×4 inch [12.7×102 mm] steel flat, and edges 133, which are ½"[12.7 mm] thick steel, give the guide rigidity, and they form a channel to prevent the wood board from escaping out the sides of the machine. To allow access through the guide weldment during calibration procedures, the guide plate 132 does not cover the whole width between the edges 133. Guides built as described have been found helpful in reducing mechanical shock and vibration and hence in reducing measurement errors due to inertial noise in the force measurement.

When the movable clamp carriages are in the up position, it will be seen that the lower guards 104 in first, second and third clamp units together with edges 133 of second and third board guides provide an almost continuous lateral channel from infeed end of the first clamp unit to the outfeed end of the third clamp unit. This channel is 12.5 inches [318 mm] wide and, therefore, the second clamp rollers, whose roller shells 33 have length 12 inches [305 mm], fit between the guards 104 when clamping thin wood boards. First clamp roller shells 77, second clamp roller shells 33 and guide plates 132 of both second and third board guides form a vertical channel for the wood boards over substantially the same length of the apparatus as the lateral channel.

Usually during operation, wood boards will be guided at the infeed of the apparatus so that they will travel through the machine on center and thus be guided by the guide plates 132 of the second and third board guides. However, it has been found that guide wings 135 at the downstream ends of the guides make the design more forgiving and allow boards to travel off-center down either side with only negligible effect on the measurement. Guide wings are shown only on the downstream end of the board guide in FIG. 25; however, in some cases where the incidence of off-center boards is severe, guide wings can be 5put also on the upstream end for smoother operation. In the event a narrow wood board travels through the machine off-centered so that it completely misses guide plate 132, then it may strike the cross tubes 134. Hence, it is important that the cross tubes are shaped as shown or otherwise are fitted with ramping means to prevent the board from bluntly striking the cross tubes and either bending them, breaking the board or jamming in the apparatus.

Refer to FIG. 27 for an end elevation view looking upstream at the first clamp unit with the second board guide installed, but with some other components absent. It will be useful to refer also to FIGS. 24–26 for views of the board guide, where FIG. 26 is a side elevation view showing board guide end plate 136, board guide supports 137, resilient interface 138 and hub 139. Board guide end plate 136 is fastened to the first clamp unit by screws 140 through elongated slots 141. The slots allow a small amount of vertical elevation adjustment so that the clearance from the wood board to the second board guide may be adjusted. It has been found that carefully setting this clearance reduces bandwidth requirements of amplifiers 15 and 24 of FIG. 2. Board guide supports 137 are welded to board guide endplate 136 and fastened by screws 142 and washers 143 through resilient interface 138 and hub 139 to the guide weldment 145.

The same arrangement is used to mount both ends of the second and the third board guides. However, in one end of each of these board guides, the resilient interface fills a rectangular shaped hole in the board guide supports, while in the other end, the resilient interface 138 is shorter in the longitudinal direction, resulting in a translational degree of freedom of the guide weldment in directions 144 relative to the board guide supports 137. In the first test section, where the second board guide is attached to the movable clamp carriages of the first and second clamp units, this translational degree of freedom is essential to allow these movable clamp carriages to move up and down at opposite, slightly off-vertical angles without binding. In the second test section, where the third board guide is attached to the fixed clamp carriages of the second and third clamp units, the translational degree of freedom allows fastening of the board guide to the fixed clamp carriages without any special means for adjusting the distance between fastening points.

Refer now to FIGS. 20–23 for illustrations of a rigid connective device 146 called a bridge frame. The purpose of the bridge frame is to provide a means tier mounting the second deflection means 20 in a way that is rigidly referenced to the second test section reference plane.

The bridge frame is suspended longitudinally between axes 147 of the second reference rollers 148 in the apparatus and is rotatably connected at these suspension points with bearings. At one end., the suspension also has a translational degree of freedom that is essential to accommodate without binding the opposite, slightly off-vertical motion of the movable clamp carriages in the second and third clamp units on which the bridge is suspended. FIG. 20 is a plan view of the second test section reference rollers 148, and parts of the movable clamp carriages 67 in the second and third clamp units as well as the bridge frame 146 and second deflection means 20.

FIG. 23 is an expanded view of one of the two suspension points at the end of the bridge frame where translation is allowed. The protective large diameter washer 154 has been removed to illustrate better the bearing arrangement. A hard polished steel hub 149 fits tightly over reference roller shaft 199 and forms at its outer diameter a bearing surface for bearing member 151. Bearing member 151 is machined from oil impregnated bronze bearing material available, for example, from Symmco Inc., Sykesville, Pa. Bearing member 151 has an inner diameter that fits over hub 149. The outer surface of bearing member 151 is machined to a square shape, to fit within the upper and lower surfaces of a rectangular hole machined into a first bridge wing plate 152. Chamfered corners 155 allow milling with reasonable radius in the corners of the rectangular shaped hole in the first bridge wing plate 152. Clearance in directions 153 allows relative translational freedom in these directions between the bridge wing plate and the reference roller shaft 199.

Thus, at one reference roller axis for bridge frame suspension, first bridge wing plates 152 have both rotational and translational degrees of freedom in their suspension. At the other reference roller axis, the bridge frame is suspended by second bridge wing plates 156 with only a rotional degree of freedom. Although detail is not shown in the figures, the only difference in construction is that round holes, which accept round bronze bearing members, are machined in the second bridge wing plates; whereas, rectangular holes, which accept square bronze bearing members, are machined in the first bridge wing plates. In the preferred embodiment, the translational degree of freedom is located at the reference roller in the third clamp unit.

The bridge wing plates 152 and 156, side channel weldments 157, and cross channel members 59 are screwed together into a rigid framework. Each side channel weldment 157 has a 10 inch [254 mm] steel channel member with a plate folded into the channel at its ends and welded into the open face of the channel to close the channel and make it behave rigidly in torsion as a box tube. At each end, a flat plate is welded so that the side channel weldment can be rigidly fastened by screws to the bridge wing plates. A mounting plate 158 is centrally located along the side channel weldment and welded to it, to provide an adjustable attachment of the second deflection means 20.

Cross channel members 59 for the bridge frame are identical in construction to cross channel members 59 for the main frame, reference FIG. 3, and are rigidly fastened by threaded fasteners to the side channel weldments 157.

The result is a bridge frame that is rigid longitudinally in its suspension between axes of the second reference rollers and rigid in torsion and in bending at its attachment points for the deflection means.

First 13 and second 20 deflection means are identical except for details that will be discussed. There are a number of methods that can provide acceptable deflection means. FIG. 2 can be interpreted as showing the use of a skid plate to press against the lumber, which is an alternative embodiment of this invention.

The design of the second deflection means, which is illustrated in FIGS. 16–19 and in FIGS. 20–22, solves several problems, as will become apparent with further description.

The second deflection means is comprised of a load roller having load roller shell 161 and shaft 198, rigid load roller support having caps 159, shaft supports 160 and I-beam weldment 162, rigid reaction member 163, four flexure spring elements 166, accelerometer hardware 176–178 and adjusting means 173–174, 179–189 for adjusting the distance between the load roller assembly and the rigid reaction member, the load roller assembly being comprised of the load roller and rigid load roller support.

The load roller is identical in construction to the first clamp roller shown in FIG. 10, with the following exceptions. There are no sprockets attached to the load roller shell, and the load roller shell 161 and shaft 198 are not as long as the roller shells and shafts of the clamp rollers. The fitup and assembly of the load roller shell to bearings and shafts is identical with that for the clamp rollers, and the bearings are identical.

The load roller shaft is fastened securely at its ends to shaft supports 160 by tightening caps 159 with screws 80 in much the same way that clamp roller shafts are fastened to the clamp carriage. Shaft supports are themselves rigidly fastened to end plates welded to an I-beam weldment 162 fabricated from ½×4 inch [12.7×102 mm] steel flat for the flanges and ½×3 inch [12.7×76.2 mm] steel flat for the web. On one flange of the I-beam weldment, a mounting plate 164 is welded so that force measuring load cell 165 can be mounted. A device that has been found to work very well is the Model 1210AO load cell manufactured by Interface Inc. of Scottsdale AZ. A portion of the web is removed from the I-beam weldment in the vicinity of the load cell mounting hole, so that a load cell attachment screw 172 can be inserted. The load roller assembly just described is rigid, with all vibration modes having frequencies well above 200 Hz.

It is necessary to suspend the load roller assembly on a reaction member 163 so that a force increment applied to the load roller in the direction of loading by the wood board is felt linearly as a load increment at the load cell. Further, because it is desired to allow the wood board to pass through the machine anywhere within its throat and not constrain it to pass directly down the machine center, the load applied to the load cell should be the same regardless of where along the length of the load roller the load is applied.

The apparatus disclosed here achieves these goals by fastening the load roller assembly to the reaction member through four flexure spring elements 166, each made of 0.094 inch [2.39 mm] thick×4 inch [102 mm] wide×5 inch [127 mm] long clock spring steel and having three attachment holes in each end. Elongated thick washers 168 with tightening screws anchor the flexure elements firmly at their one end in place against caps 159 and shaft supports 160 of the load roller assembly and at their other end against mounting plates 169 that are fastened to reaction member extensions 170. The attachments take up a length of flexure spring element equal to one inch [25.4 mm] at each end, leaving a 3 inch [76.2 mm] length for flexing. The spring elements are spaced in the direction of loading 171 by a distance 8.75 inches [222 mm], and two of the elements are attached at each end of the load roller assembly.

The reaction member 163 is an I-beam weldment made from ½×4.5 inch [12.7×114 mm] steel flat for the flanges and ½×4 inch [12.7×102 mm] steel flat for the web. The web has a slot of about 1.63 inch [41 mm] width removed from its center, and a hole is bored through a flange of the reaction member at its center. A hard steel, right-circular cylinder 174 of 1.5 inch [38.1 mm] diameter is captured in that space by a pair of opposed steel friction plates 173, one on each side of the I-beam web. One friction plate is welded to the web, and the other is fastened to the welded-on plate through the web with screws 179. Cylindrical cutouts on the web side of the opposed friction plates grip the cylinder by friction when the plates are tightened by means of screws 179.

A load cell button 172, fabricated by facing the head of a hard screw and screwing it into the load cell 165, presses against the cylinder 174. The cylinder 174 is adjustable in the direction 171 of the applied force, or opposite to it, by adjustment means 175 built into the reaction member 163. By adjusting the position of cylinder 174, the distance between the load roller assembly and the reaction member can be adjusted, thereby changing the deflection of the flexure elements and changing the amount of load applied to load cell 165 at the interface between the load cell button 172 and the cylinder 174. The adjustment should be made so there is a compressive preload at this interface for all operating conditions. This compressive preload can be subtracted out during calibration by zero (tare) adjustment of the corresponding amplifier 15 or 24.

The geometry as described ensures that a load applied in direction 171 will cause the same force on the load cell regardless of where the load is applied along the length of the load roller. Further, the size of the elements chosen ensures that modes of vibration have frequencies well above 200 Hz.

Referring now also to FIG. 5, note that during operation, the movable clamp carriages move down and up slightly against pressure from air powered actuators 88 and 64 as wood boards enter and leave the spaces between the fixed and movable clamp rollers. In the second test section, this motion is transferred by the bridge frame 146 to the second deflection means 20, which contains a load roller assembly pressing against a load cell. Acceleration of the load roller assembly, which has mass, causes an inertial force to be applied to the load cell. This inertial force is not related to the bending stiffness of the wood board and leads to an inertially caused error component in the signal. Accelerometer 176 mounted to flange 201 of I-beam weldment 162 through insulating blocks 177 and mounting screws 178 senses accelerations in the direction 171 and opposite to it for the purpose of removing inertially caused measurement errors.

FIGS. 18 and 19 show detail of the adjustment means, the load cell mounting, and the accelerometer and its mounting. Plates 180–182 are fastened to flange 206 of reaction member 163 by screws 183. Plates 181 and 182 are fastened together by screws 184. The head of adjustment socket head cap screw 185 is captured in counter-bored cavity 186 at interface of plates 181 and 182. Hole 187 allows access of hex key to rotate screw 185. Adjustment screw 185 is threaded into wedge element 189, which translates horizontally in the view of FIG. 19 upon rotation of the screw. An inclined plane face of wedge element 189 causes a mating face of wedge element 188 to translate upward as screw 185 is advanced. The thread pitch of screw 185 is 20 threads/inch [0.787 threads/mm], and the slope of the inclined plane surfaces is 1 in 8; hence the wedge element 188 and right circular cylinder 174, which is loosely pinned to it, move vertically at the rate $\frac{1}{160}$ inch/turn [0.159 mm/turn]. To adjust the space between the load roller assembly and the reaction member, first one loosens the screws 179 and then adjusts the screw 185 by means of a hex key inserted through access hole 187. Although this adjustment is primarily for adjusting the preload force on the load cell, it can be used also to effect small changes in adjustment of deflection relative to the second test section reference plane.

Now referring to FIGS. 17 and 20–22, mounting plates 158 are welded to the bridge frame. The deflection means 20 is fastened to the bridge frame 146 by screws 190 that fasten through slotted holes 191 in the mounting plates 169 and reaction member extensions 170 to the plates 158. Adjustment plates 192–193 are fastened to plates 158 and 170 by means of screws 194 and 195. Adjustment screws 196 and lock nuts 197 are used to adjust the elevation of the second deflection means with respect to the bridge frame and, therefore, with respect to the second test section reference plane. Adjustment by screws 196 and lock nuts 197 does not affect the preload force caused by the flexure springs.

Thus, the second deflection means is rigidly mounted in the second test section at the center of the bridge frame 146.

The orientation of the second deflection means 20 is such that the deflection reference plane, which contains both the load roller axis and the load cell axis is perpendicular to the test section reference plane.

The above discussion for the second deflection means 20 applies to the first deflection means 13, except that the orientation of the first deflection means is upside down from the second. Also, the first deflection means mounts to the apparatus main frame because the first reference rollers, and hence the first test section reference plane, are themselves referenced to fixed clamp carriages that are fixed to the main frame. Consequently, if frame vibration frequencies are sufficiently high, inertial noise is not a problem, and an accelerometer is not needed for the first test section. As a final difference, to allow welded attachment to the main frame, the mounting plates for the first deflection means are longer than those for the second deflection means. Screw adjustment of the position of the first deflection means relative to the main frame and hence relative to the first test section reference plane is provided in a manner similar to that provided by parts 192–197 for the second deflection means. The main frame of the apparatus contributes to the rigidity of the first deflection means much as the bridge frame contributes to the rigidity of the second deflection means.

Figure 30:
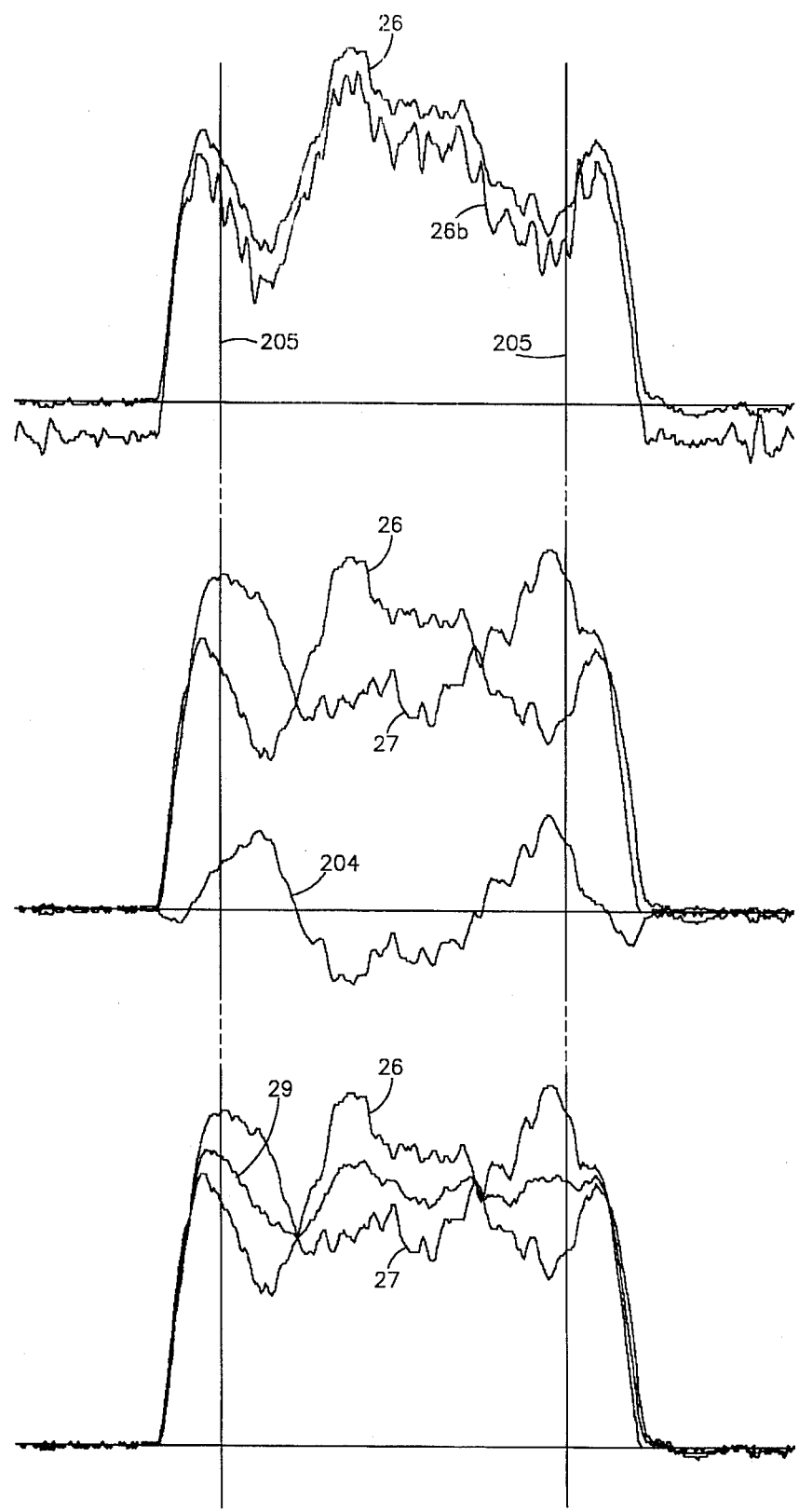
FIG. 30 illustrates resulting signals from the measurement process.

In FIG. 30, results from taking data during testing of a wood board are illustrated. It will be helpful to refer also to FIG. 2. In the upper set of curves, the second E signal 26, as a function of position along the board, is from the second test section with the measurement error from inertial noise compensated by using information coming into amplifier 24 on cable 61. The second E signal 26b was measured during another test on the same wood board but without compensation for the noise. To better illustrate the compensation for inertial noise, signal 26b has been shifted downward relative to signal 26 in the upper set of curves of FIG. 30. The center set of curves show second E signal 26, delayed first E signal 27 and local warp signal 204, which is one half the difference of signals 26 and 27 all shown as functions of position along the tested board. Signal 204 is a measure of warp at positions along the tested wood board. The lower set of curves show signal 26, signal 27 and signal 29 as functions of position along the tested board. Signal 29 is one half the sum of signals 26 and 27, i.e., the average of them. Signal 29 is the local E signal, which is a measure of the stiffness at positions along the wood board. The interval between the vertical lines 205 in FIG. 30 is the interval during which both photosensors 32 are blocked by the same wood board. The rise and fall of the signals before and after this interval illustrate the effect of the second and third board guides in causing the board to enter and exit the test spans smoothly.

In compliance with the statute, the invention has been described in language more or less specific as to structural features. It is to be understood, however, that the invention is not limited to the specified features shown, because the means and construction herein disclosed comprise a preferred form of putting the invention into effect. The invention is, therefore, claimed in any of its forms or modifications within the proper scope of the appended claims appropriately interpreted in accordance with the doctrine of equivalents.

We claim:

1. An improved apparatus, with infeed and outfeed ends, for determining bending stiffness of a wood board moving parallel to its length in a longitudinal direction from infeed to outfeed by measuring forces required to cause bending deflections in directions perpendicular to a pair of opposing faces of the wood board, comprising:

a rigid elongated main frame having a frame reference plane;

first and second test sections spaced longitudinally along the apparatus between infeed and outfeed ends;

first, second and third clamp units, spaced longitudinally along the apparatus and attached to the main frame, the first clamp unit located between the infeed end and the first test section, the second clamp unit located between the first and, the second test sections and the third clamp unit located between the second test section and the outfeed end, each clamp unit having a clamp reference plane, multiple clamp rollers arranged in a plurality of pairs with roller axes parallel to the frame reference plane and perpendicular to the longitudinal direction, clamp actuator means for applying pressure to the wood board between each pair of clamp rollers, stop means to set the space between pairs of clamp rollers when no wood board is present, drive means for applying motive force to selected clamp rollers for the purpose of transporting the wood board through the apparatus, each pair of clamp rollers meeting the wood board on its opposing faces at lines of contact, the lines of contact for each pair of clamp rollers in a clamp unit defining a plane perpendicular to the clamp reference plane of that clamp unit, the condition of perpendicularity being independent of the thickness of the wood board, the lines of contact with a wood board in each clamp unit for clamp rollers contacting the same face of the wood board defining a plane parallel to the clamp reference plane, the first, second and third clamp reference planes meeting the frame reference plane at first, second and third clamp angles and with lines of intersection of the clamp reference planes with the frame reference plane being parallel with the clamp roller axes, the first clamp angle being substantially equal to the negative of the second clamp angle, and the first and third clamp angles being substantially equal;

two first reference rollers, the first reference rollers both being on the same side of the wood board, one first reference roller being a clamp roller in the first clamp unit and the other being a clamp roller in the second clamp unit, the first reference rollers being adjacent the first test section, the lines of contact of the first reference rollers with the wood board defining both the extent of the first test section in the longitudinal direction and a first test section reference plane;

two second reference rollers, the second reference rollers both being on the opposite side of the wood board relative to the first reference rollers, one of the second reference rollers being a clamp roller in the second clamp unit and the other being a clamp roller in the third clamp unit, the second reference rollers being adjacent the second test section, the lines of contact of the second reference rollers with the wood board defining both the extent of the second test section in the longitudinal direction and a second test section reference plane;

first deflection means together with first mounting means to locate and mount the first deflection means substantially midway along the first test section, the first deflection means having a deflection reference plane oriented perpendicularly with the first test section reference plane, oriented parallel with clamp roller axes and located substantially midway along the first test section, the first mounting means including a first adjustment means for adjusting the position of the first deflection means in directions perpendicular to the first test section reference plane by an amount sufficient to contact and bend the wood board by a selected first deflection relative to the first test section reference plane;

first force measuring means to sense the force required to achieve the first deflection;

second deflection means together with second mounting means to locate and mount the second deflection means substantially midway along the second test section, the second deflection means having a deflection reference plane oriented perpendicularly with the second test section reference plane, oriented parallel with clamp roller axes and located substantially midway along the second test section, the second mounting means including a second adjustment means for adjusting the position of the second deflection means in directions perpendicular to the second test section reference plane by an amount sufficient to contact and bend the wood board by a selected second deflection relative to the second test section reference plane;

second force measuring means to sense the force required to achieve the second deflection;

first test section board guide means to guide the wood board out of the first clamp unit and into the second clamp unit;

second test section board guide means to guide the wood board out of the second clamp unit and into the third clamp unit; and timing means for matching the time required for a position on the wood board to travel from the center of the first test section to the center of the second test section;

signal processing means for processing signals from the first and second force measuring means and from the timing means to determine bending stiffness of the wood board.

2. The apparatus of claim 1, wherein the clamp rollers of each clamp unit are organized into a plurality of first clamp rollers to press on one face of the wood board and a plurality of second clamp rollers to press on the opposite face of the wood board, the first clamp rollers being supported in a fixed clamp carriage and the second clamp rollers being supported in a movable clamp carriage, the clamp actuator means acting on the movable clamp carriage in a direction to force the second clamp rollers to apply pressure against one face of the wood board and force the wood board against the first clamp rollers so as to forcibly press the wood board between corresponding first and second clamp rollers at lines of contact directly across the wood board from one another, the movable clamp carriage being constrained by clamp guide means to move by translation in only a direction perpendicular to the clamp reference plane and by rotation only about an axis substantially parallel to the axes of the clamp rollers, the purpose of this rotational degree of freedom being to allow equalization of the pressure applied by the second clamp rollers to the wood board.

3. The apparatus of claim 2, wherein each clamp roller consists of a roller shell rotatably mounted on a concentric shaft by two bearings, one near each end of the roller shell, the shaft being firmly clamped at both ends to one of either a fixed or a movable clamp carriage.

4. The apparatus of claim 3, wherein a plurality of clamp roller shells of first clamp rollers in each clamp unit are forcibly rotated about their respective axes, the rotation of each such clamp roller shell being forced by torque applied to one end of the roller shell.

5. The apparatus of claim 4, wherein the clamp roller shells of all the first clamp rollers in each clamp unit have the same diameter, are forcibly rotated, and have axes in a common plane parallel to the clamp reference plane.

6. The apparatus of claim 2, wherein a selected one of either the first or the second mounting means includes a rigid bridge frame suspended longitudinally between axes of the corresponding first or second reference rollers, the bridge frame having a bridge reference plane parallel to the corresponding test section reference plane, the selected mounting means being the one corresponding to the test section having test section reference plane defined by reference rollers that are second clamp rollers, the suspension at one end of the bridge frame having a translational degree of freedom in directions both parallel to the bridge reference plane and perpendicular to the clamp roller axes, the suspension at each end of the bridge frame having a rotational degree of freedom about its respective reference roller axis.

7. The apparatus of claim 6 additionally comprising auxiliary actuators arranged to support the weight of the bridge frame and the deflection means attached to it, the auxiliary actuators applying forces to the movable clamp carriages of the clamp units at the ends of the test section containing the bridge frame, the forces being applied in directions to compensate for the forces applied to these movable clamp carriages by weight of the bridge frame and the attached deflection means.

8. The apparatus of claim 1, wherein each of the first and second deflection means comprises:

a load roller assembly comprising a load roller for forcing the corresponding first or second deflection on the wood board and a rigid load roller support means, the load roller having its axis in a deflection reference plane and parallel to clamp roller axes, the load roller rotatably supported about its axis by the load roller support means;

a rigid reaction member;

the load roller support means and the reaction member being configured to allow interposing a force measuring means for measuring a force applied between them in directions in the deflection reference plane that are perpendicular to the load roller axis;

attachment means for fastening the rigid reaction member to the corresponding first or second mounting means;

a plurality of spaced flexure elements connecting the load roller support means to the rigid reaction member in a manner that allows a single elastically restrained translational degree of freedom between the load roller support means and the rigid reaction member, the directions of translation being in the deflection reference plane and perpendicular to the load roller axis, the spacing and geometry of the flexure elements and the rigidity of the load roller support means and the reaction member when mounted to the apparatus with corresponding first or second mounting means being sufficient to prevent any but negligible motion either in translation or in rotation of the load roller support means and reaction member relative to one another except for the elastically restrained translational degree of freedom; and the deflection means when mounted to the apparatus and assembled with the force measuring means in place, having negligible motion of any components relative to one another except for rotation of the load roller about its axis, so that the deflection means behaves as a rigid body, except for rotation of the load roller about its axis, the rigid body having no modes of vibration below the frequency content of changes in stiffness of the wood board as it travels through the apparatus, and so that a force applied to the load roller in a direction perpendicular to the corresponding test section reference plane will be sensed as substantially the same value independently of where, in the axial direction along the load roller, the force is applied.

9. The apparatus of claim 8 additionally comprising an adjustment means for effecting a change in the distance between each load roller assembly and corresponding reaction member, the adjustment means comprising first and second movable members within a support structure, an adjustment screw attached to the first movable member, the first movable member having as one surface an inclined plane, the inclined plane of the first movable member being in contact with an opposed inclined plane surface on the second movable member, with translation of the first movable member effecting translation of the second movable member in a direction perpendicular to the translation of the first movable member and perpendicular to the corresponding test section reference plane.

10. The apparatus of claim 8 wherein each load roller consists of a roller shell rotatably mounted on a concentric shaft about two bearings, one near each end of the roller shell, the shaft being clamped firmly at both ends to the load roller support means.

11. The apparatus of claim 2, wherein the stop means for each clamp unit comprises:

a plurality of at least three fixed reference points on one of either the movable or fixed clamp carriages;

a corresponding plurality of adjustable reference points on the other of the movable or fixed clamp carriages; and a corresponding plurality of transfer means for transferring and interfacing the fixed reference points with the adjustable reference points and controlling the distance between the movable clamp carriage and the fixed clamp carriage when the clamp actuator means is active with no wood board in the apparatus, the fixed reference points, adjustable reference points and transfer means arranged so that the inspection and adjustment of this distance is in a location convenient for an operator.

12. The apparatus of claim 11 wherein the plurality of fixed reference points is exactly four;

each fixed reference point is attached near a peripheral corner of the movable clamp carriage;

the corresponding adjustable reference point is in one-to-one correspondence with the fixed reference point, the adjustable reference point is attached near a peripheral corner of the fixed clamp carriage and aligned with its corresponding fixed reference point, the adjustable reference point being adjustable in directions perpendicular to the clamp reference plane; and the corresponding transfer means is in one-to-one correspondence with the fixed and adjustable reference points, the transfer means comprising a push rod attached to the fixed clamp carriage and longitudinally aligned with its corresponding fixed and adjustable reference points, the attachment to the fixed clamp carriage allowing free longitudinal motion of the push rod in a direction perpendicular to the clamp reference plane, whereby the motion of the movable clamp carriage toward the fixed clamp carriage in the absence of a wood board is arrested by the fixed reference points pushing on corresponding transfer means rods and thence against adjustable reference points.

13. The apparatus of claim 11 additionally comprising resilient material in one or more of the plurality of transfer means, the plurality of fixed reference points or the plurality of adjustable reference points.

14. The apparatus of claim 2, wherein each of the first test section board guide means and second test section board guide means comprises:

a guide plate with leading and trailing ends oriented longitudinally between the clamp units at the ends of the test section, the guide plate spaced from the wood board at a transverse location on the side of the wood board opposite from the deflection means;

attachment means for rotatably attaching the guide plate at its ends to clamp carriages on the side of the wood board opposite from the clamp carriages containing the test section reference rollers;

the guide plate having a shape which locates its middle away from the deflection means for the corresponding test section sufficient to clear a uniform straight wood board that is in contact with the corresponding reference rollers and the deflection means, the angle of the guide plate at its leading end relative to the frame reference plane is at least as great in the same direction as the clamp angle for the clamp carriage to which the leading end guide plate is rotatably attached, and so that the angle of the guide plate at its trailing end relative to the frame reference plane is at least as great in the same direction as the clamp angle for the clamp carriage to which the trailing end of the guide plate is attached;

the guide plate at one of either the leading or the trailing end having a translational degree of freedom in a direction substantially parallel to the clamp reference plane for the clamp at that end and 15. The apparatus of claim 14, wherein the attachment means for attaching the ends of the guide plates for each of the first test section board guide means and second test section board guide means additionally comprises a resilient interfacing material.

16. The apparatus of claim 2 additionally comprising infeed board guide means to guide the wood board into the first clamp unit.

17. The apparatus of claim 16 wherein the infeed board guide means comprises:

a fixed guide plate located on the same side of the wood board as and referenced to the fixed clamp carriage of the first clamp unit;

a movable guide plate rotatably supported on an axis parallel to the clamp roller axes and located on the opposite side of the wood board as the fixed guide plate; and actuator means to force and hold the movable guide plate in one of two positions, one being a closed position used in operation for guiding the wood board into the first clamp unit, and one being an open position used during calibration or when clearing wood boards in the event they jam in the apparatus.

18. The apparatus of claim 1 additionally comprising signal processing means for processing signals from the first and second force measuring means and from the timing means to measure warp of the wood board.

19. The apparatus of claim 1, wherein each of the first and second deflection means comprises a skid plate assembly comprising:

a skid plate for forcing the corresponding first or second deflection on the wood board the skid plate having a cylindrical surface with axis in a deflection reference plane and parallel to the frame reference plane;

a rigid reaction member;

the skid plate and the reaction member being configured to allow interposing a force measuring means for measuring a force applied between them in directions in the deflection reference plane that are perpendicular to the skid plate axis;

attachment means for fastening the rigid reaction member to the corresponding first or second mounting means;

a plurality of spaced flexure elements connecting the skid plate to the rigid reaction member in a mariner that allows a single elastically restrained translational degree of freedom between the skid plate and the rigid reaction member, the directions of translation being in the deflection reference plane and perpendicular to the skid plate axis, the spacing and geometry of the flexure elements and the rigidity of the skid plate axis and the reaction member when mounted to the apparatus with corresponding first or second mounting means being sufficient to prevent any but negligible motion either in translation or in rotation of the skid plate and reaction member relative to one another except for the elastically restrained degree of freedom; and the deflection means when mounted to the apparatus and assembled with the force measuring means in place, having negligible motion of any components relative to one another so that the deflection means behaves as a rigid body, the rigid body having no modes of vibration below the frequency content of changes in stiffness of the wood board as it travels through the apparatus, and so that a force applied to the skid plate in a direction perpendicular to the corresponding test section reference plane will be sensed as substantially the same value independently of where, in the axial direction along the skid plate, the force is applied.

* * * * *